US011337835B2

(12) United States Patent
Stankus et al.

(10) Patent No.: US 11,337,835 B2
(45) Date of Patent: May 24, 2022

(54) SHAPE MEMORY BIORESORBABLE POLYMER PERIPHERAL SCAFFOLDS

(71) Applicant: ABBOTT CARDIOVASCULAR SYSTEMS INC., Santa Clara, CA (US)

(72) Inventors: John J. Stankus, Campbell, CA (US); Hugh Zhao, Pleasanton, CA (US); Mikael Trollsas, San Jose, CA (US); Syed Faiyaz Ahmed Hossainy, Hayward, CA (US); Michael H. Ngo, San Jose, CA (US); Yunbing Wang, Sunnyvale, CA (US); Benjamyn Serna, Gilroy, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 261 days.

(21) Appl. No.: 16/674,607

(22) Filed: Nov. 5, 2019

(65) Prior Publication Data
US 2020/0060851 A1 Feb. 27, 2020

Related U.S. Application Data
(63) Continuation of application No. 15/588,514, filed on May 5, 2017, now Pat. No. 10,500,076, which is a (Continued)

(51) Int. Cl.
*A61F 2/86* (2013.01)
*A61F 2/915* (2013.01)
(Continued)

(52) U.S. Cl.
CPC ............... *A61F 2/86* (2013.01); *A61F 2/915* (2013.01); *A61L 31/041* (2013.01); *A61L 31/06* (2013.01);
(Continued)

(58) Field of Classification Search
CPC ........ A61F 2/86; A61F 2/82; A61F 2002/821; A61F 2002/823; A61F 2/89; A61F 2/90;
(Continued)

(56) References Cited

U.S. PATENT DOCUMENTS 5,163,952 A   11/1992  Froix
5,670,161 A    9/1997  Healy et al.
(Continued)

FOREIGN PATENT DOCUMENTS

EP    0809981    12/1997
EP    1472301     9/2013
(Continued)

OTHER PUBLICATIONS

International Search Report and Written Opinion for PCT/US2013/033375, dated Oct. 4, 2013, 11 pgs.
(Continued)

*Primary Examiner* — Wade Miles
(74) *Attorney, Agent, or Firm* — Squire Patton Boggs (US) LLP

(57) ABSTRACT

Bioabsorbable scaffolds having high crush recoverability, high fracture resistance, and reduced or no recoil due to self expanding properties at physiological conditions are disclosed. The scaffolds are made from a random copolymer of PLLA and a rubbery polymer such as polycaprolactone.

1 Claim, 15 Drawing Sheets

Related U.S. Application Data continuation of application No. 14/603,087, filed on Jan. 22, 2015, now Pat. No. 9,668,894, which is a continuation of application No. 13/555,903, filed on Jul. 23, 2012, now Pat. No. 8,968,387.

(51) Int. Cl.
*A61L 31/04* (2006.01)
*A61L 31/14* (2006.01)
*A61L 31/16* (2006.01)
*A61L 31/06* (2006.01)

(52) U.S. Cl.
CPC ............ *A61L 31/14* (2013.01); *A61L 31/148* (2013.01); *A61L 31/16* (2013.01); *A61F 2002/91508* (2013.01); *A61F 2002/91541* (2013.01); *A61F 2002/91558* (2013.01); *A61F 2210/0019* (2013.01); *A61F 2230/006* (2013.01); *A61F 2230/0054* (2013.01); *A61F 2230/0056* (2013.01); *A61F 2250/001* (2013.01); *A61L 2400/16* (2013.01)

(58) Field of Classification Search
CPC .. A61F 2/91; A61F 2/915; A61F 2002/91508; A61F 2002/91516; A61F 2002/91525; A61F 2002/91533; A61F 2002/9155; A61F 2002/91558; A61F 2002/91566; A61F 2002/91575; A61F 2002/91583
See application file for complete search history.

(56) References Cited

U.S. PATENT DOCUMENTS

| | | | |
|---|---|---|---|
| 5,756,651 A | 5/1998 | Chen et al. | |
| 5,962,007 A | 10/1999 | Cooper et al. | |
| 5,968,052 A | 10/1999 | Sullivan, III et al. | |
| 6,004,328 A | 12/1999 | Solar | |
| 6,245,103 B1 | 6/2001 | Stinson | |
| 6,281,262 B1 | 8/2001 | Shikinami | |
| 6,338,739 B1 | 1/2002 | Datta et al. | |
| 6,368,346 B1 | 4/2002 | Jadhav | |
| 6,500,204 B1 | 12/2002 | Igaki | |
| 6,991,647 B2 | 1/2006 | Jadhav | |
| 7,066,952 B2 | 6/2006 | Igaki | |
| 7,070,615 B1 | 7/2006 | Igaki | |
| 7,365,133 B2 | 4/2008 | DesNoyer et al. | |
| 7,410,498 B2 | 8/2008 | Penhasi | |
| 7,731,740 B2 | 6/2010 | LaFont et al. | |
| 7,959,942 B2 | 6/2011 | Cottone | |
| 8,309,137 B2 | 11/2012 | Hissink et al. | |
| 8,968,387 B2 | 3/2015 | Stankus et al. | |
| 9,668,894 B2 | 6/2017 | Stankus et al. | |
| 2001/0029398 A1 | 10/2001 | Jadhav | |
| 2002/0087123 A1 | 7/2002 | Hossainy et al. | |
| 2003/0083732 A1 | 5/2003 | Stinson | |
| 2003/0195611 A1 | 10/2003 | Greenhalgh et al. | |
| 2004/0034405 A1 | 2/2004 | Dickson | |
| 2004/0098100 A1 | 5/2004 | Williams et al. | |
| 2004/0143317 A1 | 7/2004 | Stinson et al. | |
| 2004/0143322 A1 | 7/2004 | Litvack et al. | |
| 2004/0210304 A1 | 10/2004 | Sequin et al. | |
| 2004/0236409 A1 | 11/2004 | Pelton et al. | |
| 2005/0232967 A1 | 10/2005 | Kladakis et al. | |
| 2006/0058863 A1 | 3/2006 | LaFont et al. | |
| 2006/0142736 A1 | 6/2006 | Hissink et al. | |
| 2006/0224226 A1 | 10/2006 | Huang et al. | |
| 2006/0265048 A1 | 11/2006 | Cheng et al. | |
| 2007/0162103 A1 | 7/2007 | Case et al. | |
| 2007/0283552 A1 | 12/2007 | Gale et al. | |
| 2008/0140189 A1 | 6/2008 | Nguyen et al. | |
| 2008/0147165 A1 | 6/2008 | Hossainy et al. | |
| 2008/0269745 A1 | 10/2008 | Justin | |
| 2008/0275537 A1 | 11/2008 | Limon | |
| 2009/0111787 A1 | 4/2009 | Lim et al. | |
| 2009/0149940 A1 | 6/2009 | Wang et al. | |
| 2009/0304770 A1 | 12/2009 | Lewis et al. | |
| 2010/0228337 A1 | 9/2010 | Milisav | |
| 2010/0249896 A1 | 9/2010 | Sugimoto et al. | |
| 2010/0256728 A1 | 10/2010 | Rea Peterson | |
| 2011/0066222 A1 | 3/2011 | Wang et al. | |
| 2011/0066225 A1 | 3/2011 | Trollsas et al. | |
| 2011/0190871 A1 | 8/2011 | Trollsas et al. | |
| 2011/0190872 A1 | 8/2011 | Anukhin et al. | |
| 2011/0196475 A1 | 8/2011 | Kitaoka et al. | |
| 2011/0270383 A1 | 11/2011 | Jow et al. | |
| 2012/0029618 A1 | 2/2012 | Tischler et al. | |
| 2012/0073733 A1 | 3/2012 | Ngo et al. | |
| 2012/0271396 A1 | 10/2012 | Zheng et al. | |
| 2012/0290073 A1 | 11/2012 | Wang | |
| 2013/0085563 A1 | 4/2013 | Stankus et al. | |
| 2013/0131778 A1 | 5/2013 | Igaki et al. | |
| 2013/0150943 A1 | 6/2013 | Zheng et al. | |
| 2013/0261736 A1 | 10/2013 | Kleiner | |
| 2013/0338762 A1 | 12/2013 | Jayasinghe et al. | |
| 2014/0018903 A1 | 1/2014 | Eli et al. | |

FOREIGN PATENT DOCUMENTS

| | | |
|---|---|---|
| JP | 2004-513697 | 5/2004 |
| JP | 2010-184128 | 8/2010 |
| JP | 2011-502195 | 1/2011 |
| WO | WO 02/39875 | 5/2002 |
| WO | WO 2009/045808 | 4/2009 |
| WO | WO 2011/094621 | 8/2011 |
| WO | WO 2012/011269 | 1/2012 |
| WO | WO 2013/003644 | 1/2013 |
| WO | WO 2013/052183 | 4/2013 |

OTHER PUBLICATIONS

Notice of Reasons for Rejection dated Jan. 20, 2017 in Japanese Patent Application No. 2015-524251, 8 pages.
Van Vlack, Lawrence H., "Elements of Materials Science and Engineering", pp. 270-271 (1989).
Xu et al., "Thermal Responsive Shape Memory Polymers for Biomedical Applications", Biomedical Engineering-Frontiers and Challenges, pp. 125-142 (2011).

| Attribute | FIGS. 3,4 and 5A | V2 | V23/008 | V23/014 |
|---|---|---|---|---|
| | | \multicolumn{3}{c}{Scaffold examples having crush recovery and reduced crimp profile} | | |
| Total length (mm) | - | 36 | 38 | 38 |
| Number of crowns | - | 9 | 9 | 9 |
| Number of links | - | 3 | 3 | 3 |
| wall thickness (in) | 235 | .008 | .008 | .014 |
| OD (mm) | - | 7 | 9 | 9 |
| Strut width (in) | 361 | 0.0085 | 0.011 | 0.011 |
| Crown width (in) | 362 | 0.0085 | 0.011 | 0.011 |
| Link width (in) | 363 | 0.007 | 0.006 | 0.006 |
| Strut length (in) | 364 | 0.071 | 0.081 | 0.081 |
| Ring height (in) | 365 | 0.057 | 0.052 | 0.052 |
| angle (deg.) | 366 | 65 | 100 | 100 |
| angle (deg.) | 367 | 67 | 95 | 95 |
| angle (deg.) | 368 | 59 | 104 | 104 |
| angle (deg.) | 368 | 57 | 104 | 104 |
| crown radius (in) | 369 | 0.0067 | 0.006 | 0.006 |
| crown radius (in) | 370 | 0.0152 | 0.017 | 0.017 |
| crown radius (in) | 371 | 0.0078 | 0.008 | 0.008 |
| crown radius (in) | 372 | 0.0163 | 0.017 | 0.017 |
| crown radius (in) | 373 | 0.0081 | 0.0081 | 0.0081 |
| crown radius (in) | 374 | 0.0166 | 0.015 | 0.015 |
| Range of Radial Strength (N/mm) | - | 0.30-0.45 | 0.30-0.45 | 0.45-0.65 |
| Range of Radial Stiffness (N/mm) | - | 0.50-0.70 | 0.50-0.70 | 0.90-1.10 |
| Range of Crush Recovery (%) at 50% pinching | - | 87-95 | 87-95 | 80-85 |

FIG 6A

| Attribute | FIGS. 2,3 & 5B | Scaffold example having crush recovery and reduced crimp profile ("V59") |
|---|---|---|
| pre-crimp diameter (mm) | - | 8 |
| scaffold length (mm) | - | 35.96 |
| number of rings | - | 16 |
| wall thickness (in) | 235 | 0.011 |
| mid strut width (in) | 261 | 0.0116 |
| inner radii (in) | 262 | 0.00025 |
| outer radii (in) | 263 | 0.01325 |
| link width (in) | 264 | 0.0115 |
| ring height (in) | 265 | 0.0589 |
| strut lenght (in) | 266 | 0.0857 |
| angle (deg) | 267 | 101 |
| angle (deg) | 268 | 105 |
| angle (deg) | 269 | 98 |
| no. of struts per ring | - | 16 |
| number of links connecting ring pairs | - | 4 |

FIG. 6B

SHAPE MEMORY BIORESORBABLE POLYMER PERIPHERAL SCAFFOLDS

This application is a continuation of U.S. application Ser. No. 15/588,514 filed May 5, 2017, which is a continuation of U.S. application Ser. No. 14/603,087 filed Jan. 22, 2015, now U.S. Pat. No. 9,668,894 issued Jun. 6, 2017, which is a continuation of U.S. application Ser. No. 13/555,903 filed Jul. 23, 2012, now U.S. Pat. No. 8,968,387 issued Mar. 3, 2015, all of which are incorporated in their entireties by reference herein.

BACKGROUND OF THE INVENTION

Field of the Invention

This invention relates polymeric medical devices, in particular, bioresorbable stents or stent scaffoldings.

Description of the State of the Art

This invention relates to radially expandable endoprostheses that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of a scaffold or scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. A medicated stent may be fabricated by coating the surface of either a metallic or polymeric scaffold with a polymeric carrier that includes an active or bioactive agent or drug. Polymeric scaffolds may also serve as a carrier of an active agent or drug. An active agent or drug may also be included on a scaffold without being incorporated into a polymeric carrier.

The stent must be able to satisfy a number of mechanical requirements. The stent must be capable of withstanding the structural loads, namely radial compressive forces, imposed on the scaffold as it supports the walls of a vessel. Therefore, a stent must possess adequate radial strength. Radial strength, which is the ability of a stent to resist radial compressive forces, relates to a stent's radial yield strength and radial stiffness around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded the stent is expected to yield more severely and only a minimal force is required to cause major deformation. Radial strength is measured either by applying a compressive load to a stent between flat plates or by applying an inwardly-directed radial load to the stent.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with stents require its presence for only a limited period of time. Once treatment is complete, which may include structural tissue support and/or drug delivery, it may be desirable for the stent to be removed or disappear from the treatment location. One way of having a stent disappear may be by fabricating a stent in whole or in part from materials that erodes or disintegrate through exposure to conditions within the body. Stents fabricated from biodegradable, bioabsorbable, bioresorbable, and/or bioerodable materials such as bioabsorbable polymers can be designed to completely erode only after the clinical need for them has ended.

The development of a bioresorbable stent or scaffold could obviate the permanent metal implant in vessel, allow late expansive luminal and vessel remodeling, and leave only healed native vessel tissue after the full absorption of the scaffold. A fully bioresorbable stent can reduce or eliminate the risk of potential long-term complications of late thrombosis, facilitate non-invasive diagnostic MRI/CT imaging, allow restoration of normal vasomotion, and provide the potential for plaque regression.

To treat peripheral vascular disease percutaneously in the lower limbs is a challenge with current technologies. Long term results are sub-optimal due to chronic injury caused by the constant motions of the vessel and the implant as part of every day life situations. To reduce the chronic injury a bioresorbable scaffold for the superficial femoral artery (SFA) and/or the popliteal artery can be used so that the scaffold disappears before it causes any significant long term damage. However, one of the challenges with the development of a femoral scaffold and especially a longer length scaffold (4-25 cm) to be exposed to the distal femoral artery and potentially the popliteal artery is the presence of fatigue motions that may lead to chronic recoil and strut fractures especially in the superficial femoral artery, prior to the intended bioresorption time especially when implanted in the superficial femoral artery.

A scaffold in the SFA and/or the popliteal artery is subjected to various non-pulsatile forces, such as radial compression, torsion, flexion, and axial extension and compression. These forces place a high demand on the scaffold mechanical performance and can make the scaffold more susceptible to fracture than less demanding anatomies. In addition to high radial strength, stents or scaffolds for peripheral vessels such as the SFA, require a high degree of crush recovery. The term "crush recovery" is used to describe how the scaffold recovers from a pinch or crush load, while the term "crush resistance" is used to describe the force required to cause a permanent deformation of a scaffold.

Therefore, an important goal for treatment of the SFA and/or the popliteal artery is the development of bioabsorbable scaffold with high radial strength, high crush recovery, and high resistance to fracture or high toughness.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

SUMMARY OF THE INVENTION

Embodiments of the present invention include a stent comprising a scaffold formed from a polymer tube configured for being crimped to a balloon, the scaffold having a pattern of interconnected struts and the scaffold having an expanded diameter when expanded from a crimped state by the balloon, wherein the scaffold attains greater than about 80% of its diameter after being crushed to at least 50% of its expanded diameter; wherein the scaffold has a radial stiffness greater than 0.3 N/mm and wherein the scaffold is made from a shape memory random copolymer of poly(L-lactide) (PLLA) and a rubbery polymer that is 0.1 to 10 wt % or molar % of the copolymer, wherein the scaffold exhibits self expanding properties at 37 deg C. in physiological conditions.

BRIEF DESCRIPTION OF THE DRAWINGS

FIGS. 6A and 6B are tables showing examples of scaffold features in accordance with aspects of the disclosure.

DETAILED DESCRIPTION OF THE INVENTION

Figure 1:
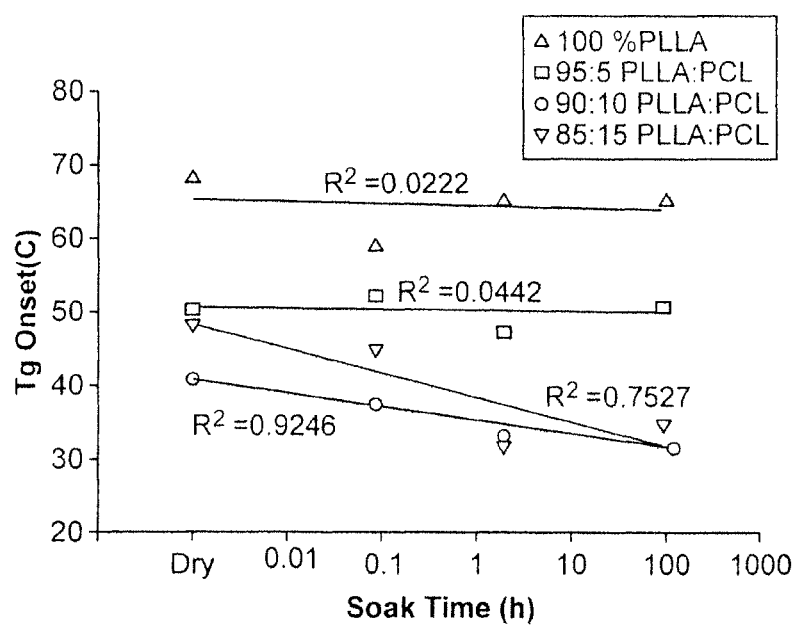
FIG. 1 depicts the Tg onset of four samples of PLLA and poly(L-lactide-co-caprolactone) (PLLA-PCL) copolymers at three molar compositions, 95:5, 90:10, and 85:15, as function of soak time in water.

The embodiments described herein are generally applicable to polymeric implantable medical devices, especially those that have load bearing portions when in use or have portions that undergo deformation during use. In particular, the methods can be applied to tubular implantable medical devices such as self-expandable stents, balloon-expandable stents, and stent-grafts.

A stent or scaffold may include a tubular scaffold structure that is composed of a plurality of ring struts and link struts. The ring struts form a plurality of cylindrical rings arranged about the cylindrical axis. The rings are connected by the link struts. The scaffold comprises an open framework of struts and links that define a generally tubular body with gaps in the body defined by the rings and struts. A thin-walled cylindrical tube of may be formed into this open framework of struts and links described by a laser cutting device that cuts such a pattern into the thin-walled tube that may initially have no gaps in the tube wall.

The scaffold may also be fabricated from a sheet by rolling and bonding the sheet to form the tube. A tube or sheet can be formed by extrusion or injection molding. The scaffold can then be crimped on to a balloon or catheter for delivery into a bodily lumen.

A stent or scaffold of the present invention can be made partially or completely from a biodegradable, bioresorbable, and bioabsorbable polymer. The stent can also be made in part of a biostable polymer. A polymer for use in fabricating stent can be biostable, bioresorbable, bioabsorbable, biodegradable, or bioerodable. Biostable refers to polymers that are not biodegradable. The terms biodegradable, bioresorbable, bioabsorbable, and bioerodable are used interchangeably and refer to polymers that are capable of being completely degraded and/or eroded into different degrees of molecular levels when exposed to bodily fluids such as blood and can be gradually resorbed, absorbed, and/or eliminated by the body. The processes of breaking down and absorption of the polymer can be caused by, for example, hydrolysis and metabolic processes.

Bioresorbable stents or scaffolds can be useful for treatment of various types of bodily lumens including the coronary artery, superficial femoral artery, popliteal artery, neural vessels, and the sinuses. In general, these treatments require the stent to provide mechanical support to the vessel for a period of time and then desirably to absorb away and disappear from the implant site. The important properties of a bioresorbable stent or scaffolding include mechanical and degradation properties. The mechanical requirements include high radial strength, high radial stiffness, minimal recoil, and high fracture toughness. The degradation properties include the absorption profile, for example, the change in molecular weight, radial strength, radial stiffness, and mass with time. Specific aspects of the absorption profile include the time that the stent maintains radial strength and radial stiffness, before starting to decrease and the total absorption time or absorption time (complete mass loss from implant site).

A stent scaffolding made from a bioresorbable polymer may be designed to maintain its radial strength and/or radial stiffness once implanted to provide mechanical support to the vessel for a prescribed time period and maintain patency of the lumen. The radial strength must be sufficiently high initially to support the lumen at a desired diameter. The period of time that the scaffold is required or desired to maintain patency depends on the type of treatment, for coronary treatment it is about 3 months. After this time period, the vessel is healed sufficiently to maintain an expanded diameter without support. Therefore, after this time period, the scaffolding may start to lose radial strength and/or radial stiffness due to molecular weight degradation. As the scaffolding degrades further, it starts to lose mechanical integrity and then experiences mass loss and eventually absorbs away completely or there are negligible traces left behind. The decrease in radial strength and radial stiffness can also be the result of mechanical fractures in certain anatomies where this is desired, or it could also be the result of a combination of the mechanical and chemical degradation.

Ideally, it is desired that once the stent support is no longer needed by the lumen, the bioresorbable scaffold should be resorbed as fast as possible while also meeting all basic safety requirements during its degradation period. Such safety requirements can include a gradual disintegration and resorption that does not allow release of fragments that could cause adverse events such as thrombosis. In this way, the stent scaffold enables the vessel healing as well as enabling the advantages mentioned herein of a bioresorbable scaffold to the greatest extent. It is desirable for a bioresorbable scaffold to have an absorption time of about 18 to 26 months for coronary vascular application, of about 12-26 months for a peripheral application (e.g., superficial femoral artery (SFA), tibial, and/or politeal artery), 18-24 months for neural applications, and less than a year for nasal applications.

With respect to radial strength and stiffness, a stent should have sufficient radial strength and/or stiffness to withstand structural loads, namely radial compressive forces, imposed on the stent so that the stent can supports the walls of a vessel at a selected target diameter for a desired time period. A polymeric stent with adequate radial strength and/or stiffness enables the stent to maintain a lumen at a desired diameter for a sufficient period of time after implantation into a vessel.

In addition, the stent should possess sufficient toughness or resistance to fracture to allow for crimping, expansion, and cyclic loading without fracture or cracking that would compromise the function of the stent. The toughness or resistance to fracture of the scaffold material can be characterized for a material by the elongation at break and for a stent by the number and degree of cracks in a scaffold during use, such as after crimping or deployment or dilation to a target diameter. These aspects of the use of the scaffold involve deformation of various hinge portions of the structural elements of the scaffold.

Some bioresorbable polymers, for example, semi-crystalline polymers, are stiff or rigid under physiological conditions within a human body and have been shown to be promising for use as a scaffold material. Specifically, polymers that have a glass transition temperature (Tg) sufficiently above human body temperature which is approximately 37° C., should be stiff or rigid upon implantation. Poly(L-lactide) (PLLA) is attractive as a stent material due to its relatively high strength and a rigidity at human body temperature, about 37° C. As shown in Table 1, PLLA has high strength and tensile modulus compared to other biodegradable polymers. Since it has a glass transition temperature well above human body temperature, it remains stiff and rigid at human body temperature. This property facilitates the ability of a PLLA stent scaffolding to maintain a lumen at or near a deployed diameter.

Other rigid bioresorbable polymers include poly(D-lactide) (PDLA), polyglycolide (PGA), and poly(L-lactide-co-glycolide) (PLGA). The PLGA include those having a mole % of (LA:GA) of 85:15 (or a range of 82:18 to 88:12), 95:5 (or a range of 93:7 to 97:3), or commercially available PLGA products identified being 85:15 or 95:5 PLGA. Rigid polymers may refer to polymers that have a Tg higher than human body temperature or within 5 deg C. of human body temperature.

TABLE 1

Comparison of properties of bioresorbable polymers.

|  | Tm (° C.) | Tg (° C.) | Tensile Strength (MPa) | Tensile Modulus (MPa) | Elongation at break (%) | Absorption Rate |
|---|---|---|---|---|---|---|
| PLLA | 175 | 65 | 28-50 | 1200-2700 | 6 | 1.5-5 years |
| P4HB | 60 | −51 | 50 | 70 | 1000 | 8-52 weeks |
| PCL | 57 | −62 | 16 | 400 | 80 | 2 years |
| PDO | $110^1$ | $-10^1$ | $1.5^{1,2}$ | $30^2$ | $35^3$ | $6-12^1$ $6^2$ |
| PGA | 225 | 35 | 70 | 6900 | <3 | 6 weeks |
| DL-PLA | Amorphous | 50-53 | 16 | 400 | 80 | 2 years |
| P3HB | 180 | 1 | 36 | 2500 | 3 | 2 years |

PLLA (poly(L-lactide);
P4HB (poly-4-hyroxybutyrate);
PCL (polycaprolactone);
PGA (polyglycolide);
DL-PLA (poly(DL-lactide);
P3HB (poly-3-hydroxybutyrate);
PDO (p-polydioxanone)
All except PDO, Martin et al., Biochemical Engineering 16 (2003) 97-105.
[1]Medical Plastics and Biomaterials Magazine, March 1998.
[2]Medical Device Manufacturing & Technology 2005.
[3]The Biomedical Engineering Handbook, Joseph D. Bronzino, Ed. CRC Press in Cooperation with IEEE Press, Boca Raton, FL, 1995.

The strength, stiffness, and the fracture toughness of such polymers can be improved through various processing methods (e.g., radial expansion and suitable choice of associated processing parameters). However, there is still strong incentive to improve upon polymers such as PLLA as scaffold materials not only for coronary applications, but to tailor it for various peripheral applications as well. In particular, such polymers may be improved upon to reduce chronic recoil inward from a deployed diameter and to reduce strut fractures due to fatigue motions imposed on scaffolds implanted in such vessels as the popliteal artery and in the superficial femoral artery.

Embodiments of the present invention include bioresorbable scaffolds with reduced risk of scaffold fracture and improved recoil property as compared to PLLA scaffolds. Embodiments include scaffolds composed of copolymers that exhibit shape memory properties and are self-reinforcing once implanted in vessel of a human patient. Shape-memory properties refer to the ability of a material to return from a deformed state (temporary shape) to an original (permanent) shape induced by an external stimulus (trigger), such as a temperature change or thermal transition. A scaffold of the present invention has a tendency return or self expand outward towards a fabricated diameter when deployed from crimped or reduced diameter.

The temperature of the thermal transition of a shape memory polymer is referred to as a transition temperature (Ttrans) which is the temperature around which a material changes from one state to another. In general, a Ttrans can be either a melting temperature (Tm) or glass transition temperature (Tg). In the present invention, the Tg of the shape memory polymer of the scaffold is the relevant thermal transition that induces shape memory behavior of an implanted scaffold. Ttrans is typically determined by differential scanning calorimetry (DSC), thermomechanical analysis (TMA) or dynamic mechanical thermal analysis (DMA). DSC measures the change in heat capacity, TMA measures the change in coefficient of thermal expansion, while DMA measures the change in elastic modulus during the thermal transition. Due to intrinsic polydispersity in molecular weights and imperfect spatial distribution of network chains, the unique thermal characteristics of a polymer should be defined as a temperature range rather than at one specific temperature. For the ease of comparison, however, a single Ttrans (Tm or Tg) value taken from the peak or midpoint of a broader transition is often reported in literature.

For a particular shape memory copolymer with specific chemical components and their composition (e.g., 95:5 PLLA-PCL), the broadness of a thermal transition may be modified in several ways. As indicated above, the broadness of Tg is a function of polydispersity in molecular weights. The polydispersity index (PDI) or heterogeneity index of a polymer, is a measure of the distribution of molecular mass in a given polymer sample. The PDI is calculated as the weight average molecular weight, Mw, divided by the number average molecular weight, Mn. Thus, the PDI can be manipulated to achieve a selected broadness of the thermal transition.

The width of thermal transition of an SMP is also dependent on the crystallinity. Crystalline segments tend to exhibit a sharp transition with a relatively narrow temperature range while amorphous segments tend to display a glass transition range tens of degrees wide. Therefore, crystallinity of the scaffold can be manipulated through processing to achieve a selected broadness of the transition. For example, the crystallinity of a particular copolymer can be adjusted through annealing which increases crystallinity.

The copolymer of the scaffold is mostly poly(L-lactide) and a small amount of rubbery polymer. The small amount of rubbery polymer together with the poly(L-lactide) exhibit shape memory behavior upon deployment in a vessel at physiological conditions. In addition, the rubbery polymer increases the fracture resistance of the scaffold which prevents or reduces fractures when the scaffold diameter changes, for example, when the scaffold is crimped from a fabricated diameter to a reduced crimped diameter or when the scaffold is expanded from the crimped diameter to a target diameter during deployment.

Physiological conditions include a temperature at or about 37 deg C. and exposure to bodily fluids, in particular, a wet or aqueous environment. A rubbery polymer refers to a polymer that is more flexible, and thus, has a lower modulus and/or greater elongation at break than a rigid polymer such as PLLA. For example, a rubbery polymer may have a tensile modulus less than 1000 MPa or less than 500 MPa and/or an elongation at break greater than 10% or greater than 50%.

The copolymer scaffolds are fabricated from copolymer tubing at a given diameter and crimped down to a reduced diameter over a catheter balloon. The crimped scaffold is deployed from the reduced diameter to a target or nominal expansion diameter in a vessel. The scaffold may be fabricated so that it exhibits an outward force at the target diameter by oversizing the scaffold (i.e., as-fabricated diameter greater than the target diameter) relative to the target diameter. The outward force is a residual force in excess of a radial outward force that maintains the lumen at the target diameter. The oversizing is advantageous due to the increased flexibility or lower modulus of the shape memory and reinforcing scaffold.

The oversized scaffold is made from a tube with a diameter greater than the target diameter. The tube may be oversized by a tubing expansion greater than the intended target diameter. The expansion also results in sufficient scaffold radial strength and stiffness to treat a stenosed artery at early duration of the implant. Due to the oversizing, the deployed scaffold applies the outward force on the vessels walls at the target diameter or a diameter slightly greater than the target diameter. The outward force is analogous to the chronic outward force applied by self-expanding stents such as nitinol stents.

The self-expanding or shape memory scaffolds of the present invention provide sufficient radial strength, radial stiffness, and recoil to provide patency to or support a vessel and at a target diameter. Additionally, the scaffolds of the present invention have a greater resistance to fracture compared to a PLLA scaffold.

At physiological conditions of 37 deg C. and hydration in blood, the bioresorbable copolymer exhibits a thermal transition which results in shape memory behavior that includes a tendency for the scaffold to self-expand, to exert an outward residual force on the vessel wall, or both. The shape memory behavior, however, acts in a time-dependent fashion so that the mechanical properties of the scaffolds such as radial strength and compression recovery are enhanced with time upon implantation. In contrast to permanent nitinol stents, the self-reinforcing bioresorbable scaffold will degrade, reducing its residual outward force with time, transform from independent load-bearing member into tissue-incorporated composite, and ultimately disappear without causing any significant chronic vascular injury.

The mechanism of controlled reduction in scaffolding property (radial strength/stiffness/strain recovery) will reduce tissue compliance (vascular compliance in case of a vascular implant) mismatch of the implanted segment. Specifically, the scaffold undergoes degradation in three phases.

In the first phase, the molecular weight is reduced primarily due to hydrolytic degradation of the polymer chains. During this first phase, the mechanical properties such as radial strength and radial stiffness change very little or not at all so that the scaffold supports the vessel at the target diameter during this phase. This allows vessel wall remodeling that will enable the vessel to support itself at the remodeled diameter once the scaffold is gone. In the second phase, mechanical properties including the radial strength and the residual outward force of the scaffold decrease. The decrease in radial strength in particular results in the transfer of the load or support of the vessel wall from the scaffold to the vessel wall. Also, in the second phase, the scaffold begins to break up due to the deterioration of mechanical properties. Prior to breaking up, the scaffold is preferably covered by tissue. In the third phase, which may overlap the second phase, the scaffold erodes, eventually completely away from the implant site. It is during the second and third phases that the vessel compliance increases gradually from that of the scaffold to that of the natural compliance of an un-scaffolded vessel at a remodeled, increased diameter. The first and second phases could also be in the order of mechanical degradation first followed by a chemical degradation.

The residual outward force of the scaffold is lower than that of the chronic outward force of a self expanding nitinol scaffold and will therefore create less arterial injury than the nitinol implant. Moreover the axial and radial flexibility provided by the disclosed pattern of the scaffold will reduce even the acute injury that would otherwise potentially occur even before any of either the chemical or mechanical degradation starts.

A PLLA scaffold has a Tg of about 60-65 deg C., and therefore, tends not to exhibit substantial shape memory properties upon expansion in a vessel. Specifically, the PLLA scaffold is expanded to a target diameter, but does not exhibit a large tendency to self expand at physiological conditions and also will not apply a residual force in excess of that for maintaining patency of the vessel. The large difference between the Tg of the scaffold and physiological conditions (e.g., 37 deg C. and wet) is responsible for the absence of a thermal transition that would provide the tendency to self expand or a residual force.

The rubbery polymer has a Tg in dry or wet conditions less than PLLA in dry or wet conditions, respectively. Therefore, the copolymer of the scaffold of the present invention has a glass transition temperature (Tg) that is lower than that of the PLLA scaffold. The reduction in the Tg of the scaffold closer to or below the physiological conditions of 37 deg C. contributes to the shape memory property upon expansion in a vessel to a target diameter. The scaffold copolymer Tg is sufficiently close to the physiological temperature for the scaffold to exhibit a tendency to self expand towards an original fabricated diameter. This tendency reduces or eliminates recoil of the scaffold. If the scaffold is oversized, then the scaffold applies a residual outward force on the vessel wall in excess of that required to maintain the target diameter of the vessel. The residual force further reduces or eliminates recoil of the scaffold.

The Tg of the copolymer of the scaffold in dry or wet conditions may be 5 to 10 deg C., 10 to 20 deg C., 10 to 30 deg C., 20 to 30 deg C., less than the Tg of the PLLA scaffold. Alternatively, the Tg of the copolymer scaffold may be 30 to 37 deg C., 37 to 50 deg C., 37 to 55 deg C., 37 to 40 deg C., 40 to 45 deg C., 45 to 50 deg C., or 50 to 55 deg C. The rubbery polymer, as a homopolymer, may have a Tg less than 37 deg C., less than 25 deg C., 0 to 25 deg C., or −70 to 0 deg C.

The inventors have observed that the Tg of the copolymer may decrease when exposed to moisture or hydrated such as by soaking in water or implanted in a physiological environment. The decrease in Tg may be attributed to the water plasticizing the polymer. Plasticizing refers generally to increasing the plasticity of a material, where plasticity or plastic deformation describes the deformation of a polymer undergoing non-reversible changes of shape in response to applied forces. Without being limited by theory, a plasticizer, in this case water, works by embedding itself between the chains of a polymer, spacing them apart (increasing the "free volume"), and thus lowering the glass transition temperature and making it softer. As a result of plasticizing, the mechanical properties of the copolymer and scaffold change, in particular, modulus of the copolymer decreases which decreases the radial stiffness. The inventors have found that the stability of Tg over time and the degree of decrease in Tg is a function of the composition of the rubbery polymer in the copolymer.

In some embodiments, the Tg of the copolymer is both stable for a selected period of time and exhibits a thermal transition providing shape memory properties to the scaffold when it is exposed to an aqueous environment or bodily fluids. The selected period of stability may be up to 4 days, up to 1 month, or up to 3 months after implantation. For example, the Tg of the copolymer may change by less than 15% after it is hydrated, either in water or in a physiological environment during such time. A stable Tg may be preferred so that the radial stiffness of the scaffold remains stable while the vessel wall is remodeling.

The Tg of a hydrated copolymer can remain stable or change by less than 15%, or more narrowly, by between 2 to 5% when the copolymer has less than a selected weight or mole percent of the rubbery polymer. Above a selected composition of the rubbery polymer, the Tg of the copolymer can change significantly over time when hydrated. FIG. 1 depicts the Tg onset of four samples of PLLA and poly(L-lactide-co-caprolactone) (PLLA-PCL) copolymers at three molar compositions, 95:5, 90:10, and 85:15, as function of soak time in water. As shown in FIG. 1, the Tg of the PLLA and 95:5 PLLA-PCL is stable over 100 hr soaking. The Tg's of the 90:10 and 85:15 PLLA-PCL, however, change significantly over the 100 hr soak time.

In some embodiments, the rubbery polymer may be 0.5 to 1%, 1 to 5%, 2 to 5%, 3-5% (by weight or molar) of the copolymer of the scaffold. In other embodiments, the rubbery polymer may be 5 to 15%, 5 to 15%, or 15 to 25% of the copolymer of the scaffold.

In general, an increase in the amount of rubbery polymer increases fracture toughness of the copolymer and the shape memory properties, which provides increased resistance to fracture of the scaffold when crimped or deployed and reduction in recoil. However, the increase in rubbery polymer may decrease the strength and modulus of the copolymer, which can reduce radial strength and radial stiffness of the scaffold. Therefore, the amount of rubbery polymer should not be too high such that the resulting scaffold does not possess sufficient radial strength or stiffness to scaffold a stenosed artery.

Many rubbery polymers that could be used to provide shape memory properties have a lower strength than PLLA. Therefore, the radial strength of the scaffold is expected to decrease as the amount of the rubbery polymer increases. For example, as shown in Table 1, polycaprolactone has a lower tensile strength than PLLA. It is preferred that the composition of the rubbery polymer in the copolymer is less than or equal to 5 or 15% (weight or molar percent) relative to PLLA of the scaffold.

However, in some treatments, the scaffold is not required to support a vessel at an increased diameter, so radial strength is less or not important. In such treatments, the scaffold may serve as a sustained drug delivery scaffold. For such applications, a flexible copolymer scaffold may be used with greater than 15% rubbery polymer, for example, 15 to 30%, 15 to 50%, or 50 to 75% rubbery polymer.

The copolymer of the scaffolds may exhibit phase separation of the rubbery polymer from the PLLA. Thus, the polymeric scaffold made of the copolymer may be composed of soft domains and hard domains. The soft domains may be dispersed throughout the hard domains. The hard domains are partially crystalline and the soft domains are mostly amorphous or completely amorphous. The thermal transition temperatures (either Tg or Tm in a physiological environment such as blood at 37 deg C.) of the soft domain may be at 37 deg C., between 37 and 47 deg C., or any temperature below 37 deg C.

The characteristic length (diameter, length, width) of the domains can be 250 nm to 5 um, or more narrowly 250 nm to 1000 nm, 100 nm to 500 nm, 500 nm to 1 μm, or greater than 1 μm.

The copolymer thermal transition for hard domains (either glass transition or melt transition in aqueous environment such as blood) may be at a temperature greater than the physiologic temperature of 37 deg C. to preserve the desired scaffold deployment dimensions and prevent subsequent creep and relaxation properties. These deployment dimensions may be provided to the copolymer scaffold during melt extrusion of the tubing and pressurized tubing expansion (described below) at a temperature greater than the Tg, but less than the Tm.

Examples of biodegradable rubbery polymers include but are not limited to polyhydroxyalkanoates (PHA), poly(4-hydroxybutyrate) (P4HB), poly(ε-caprolactone), (PCL) poly (trimethylene carbonate) (PTMC), poly(butylene succinate) (PBS), poly(p-dioxanone) (PDO), poly(ester amides) (PEA), and biodegradable polyurethanes. A preferred type of copolymer is a random copolymer of PLLA and the rubbery polymer.

The molecular weight of the shape memory copolymer of the scaffold post-sterilization may be 60 to 150 kDA, or more narrowly 80 to 100 kDa. The molecular weight of the shape memory copolymer of the scaffold pre-sterilization may be 100 to 400 kDA, or more narrowly 150 to 300 kDa.

Embodiments can also include block copolymers of the PLLA and the rubbery polymer. These block copolymers can include linear block copolymers such as diblock (AB), triblock (ABA), or, generally, multiblock copolymers (ABABA) and star block copolymers. Additional block copolymers include hyperbranched-like polymers, comblike polymers, dendrimer-like star polymers, and dendrimers.

Embodiments of the present include scaffolds made out the copolymer which is not blended with another polymer, except for small amounts of another polymer, e.g., less than 1 wt % or incidental mixing of the copolymer with a coating at the coating/copolymer interface.

Soft domains may be modified by post plasticizing the domains with plasticizers that swell, but do not dissolve the copolymer. The plasticizing will further reduce the Tg of the polymer. For example, a PLLA-PCL copolymer scaffold can be plasticized with acetone or chloroform.

As indicated above, the thermal transition of the shape memory copolymer can occur around, not necessarily only at a thermal transition Trans, for example, Tg. Therefore, the shape memory copolymer of the scaffold need not have a Tg at this temperature for the scaffold to exhibit shape memory properties. The thermal transition may have varying degrees of broadness, i.e., the thermal transition may occur within a certain ΔT below the Tg of the copolymer. The copolymer can be designed to have a selected broadness of both Tg and Tm. For example, a copolymer may be have a broad Tg and a sharp Tm for a shape memory scaffold with a Tg>37 deg C. A broad Tg or Tm may be defined as a ΔT of between 5 and 20 deg C. A narrow Tg or Tm may be defined as a ΔT of between 5 and 10 deg C. Alternatively, a copolymer may have a sharp Tm and sharp Tg for a shape memory scaffold with Tg<37 deg C.

A shape memory polymer may also exhibit more than one Tg which may occur in block copolymers or random copolymers with a high composition of rubbery polymer, e.g., greater than 15 weight percent of rubbery polymer. A sharp Tm and two independent Tg's may provide additional degrees of freedom to control the shape memory evolution of the implant.

A preferred embodiment is a scaffold made completely of the shape memory copolymers. In some embodiments, the shape memory copolymer is not blended with another polymer. The scaffold, however, may include small amounts of other additives such as antioxidants, inorganic reinforcing agents, or therapeutic agents, for example, 0.1 to 2 wt %.

Another embodiment is a blend of the copolymer and another polymer. The scaffold may further include a polymer and drug coating.

In an alternate embodiment, a PLLA scaffold may have a coating of the shape memory copolymer. The PLLA scaffold can be dip or spray coated with the shape memory polymer, for example PLLA-PCL. The coating may have a thickness of 2 to 10 microns or 10 to 20 microns. The shape memory coating may reduce or prevent PLLA crack propagation and strut separation prior to tissue coverage. The shape memory polymer may also be applied to widen the overstretch window prior to fracture for ease of physician utilization of the scaffolds.

Another advantage of the shape memory scaffold of the present invention is that physical aging that causes embrittlement of the scaffold polymer occurs over a shorter time frame than for a PLLA scaffold. In general, after fabrication, a polymer of a scaffold undergoes a process called densification that occurs over a period of time until the properties stabilize. The time it takes for the polymer to stabilize is higher for higher Tg's. At the lower Tg of the shape memory copolymer, the physical aging process is faster and stabilizes faster. For example, for a Tg between 40 and 50 deg C., the polymer is expected to be stabilized within 2 weeks when it is stored at RT, while it might take more than 1 month to stabilize at RT for polymer with Tg at about 60 deg C. As a result, the products used for implantation will have high consistency of properties.

Additionally, the crystallinity of the shape memory random copolymer of PLLA and rubbery polymer is lower than PLLA. The rubbery polymer units incorporated in the copolymer chains tend to disrupt the formation of crystalline segments. The crystallinity of the PLLA scaffold may be 45 to 55%. In contrast, the crystallinity of the shape memory copolymer scaffold may be 10 to 40% or 20 to 30%. The decreased crystallinity increases the degradation rate, as compared to a PLLA scaffold with higher crystallinity.

Stent scaffold patterns made from PLLA for SFA and popliteal applications have been designed which have high crush recovery and crush resistance. Crush recovery describes the recovery of a scaffold subjected to a pinch or crush load. Specifically, the crush recovery can be described as the percent recovery to the scaffold pre-crush shape or diameter from a certain percent crushed shape or diameter. Crush resistance is the minimum force required to cause a permanent deformation of a scaffold.

The crush recoverable PLLA scaffolds are disclosed in US2011/0190872, US2011/0190871, and U.S. patent application Ser. No. 13/549,366. These scaffolds attain greater than about 80% of its diameter after being crushed to at least 50% of its expanded diameter. The scaffolds also have a radial stiffness greater than 0.3 N/mm. Such scaffolds also have a normalized radial strength of at least 0.4 N/mm. The inventors have found a scaffold for use in peripheral application should have these minimum values of radial stiffness and radial strength.

Embodiments of the present invention further include bioresorbable scaffolds that in addition to high crush recovery, the selected radial stiffness and radial strength, also possess high resistance to fracture and self expanding properties that reduce or eliminate recoil upon deployment. These embodiments include the previously disclosed crush recoverable scaffolds and additional crush recoverable scaffolds disclosed herein made from the shape memory copolymer disclosed herein. The inventors have found that a suitable combination of scaffold and shape memory copolymer can result in a scaffold having desired performance characteristics.

The scaffolds of the present invention for peripheral (SFA) applications usually have lengths of between about 36 and 40 mm or even between 40 and 200 mm when implanted in the superficial femoral artery, as an example. The scaffold for the SFA applications may have a pre-crimping diameter of between 5-10 mm, or more narrowly, 6-8 mm. The scaffold for SFA may have a wall thickness of about 0.008" to 0.014" and configured for being deployed by a non-compliant or semi-compliant balloon, e.g., 6.5 mm diameter, from about a 1.8 to 2.2 mm diameter (e.g., 2 mm) crimped profile. The SFA scaffold may be deployed to a diameter of between about 4 mm and 10 mm, or more narrowly, 7 to 9 mm.

These crush recoverable copolymer scaffolds can attain greater than about 80% of their diameter after being crushed to at least 50% of its expanded diameter. Additionally, such crush recoverable copolymer scaffolds have a normalized radial strength, as measured by techniques described herein and in cited applications, of greater than about 0.3 N/mm, or between about 0.3 and 1.2 N/mm or between about 0.3 and 1.2 N/mm, and a radial stiffness of greater than about 0.3 N/mm or between about 0.3 and 2 N/mm.

Figure 2:
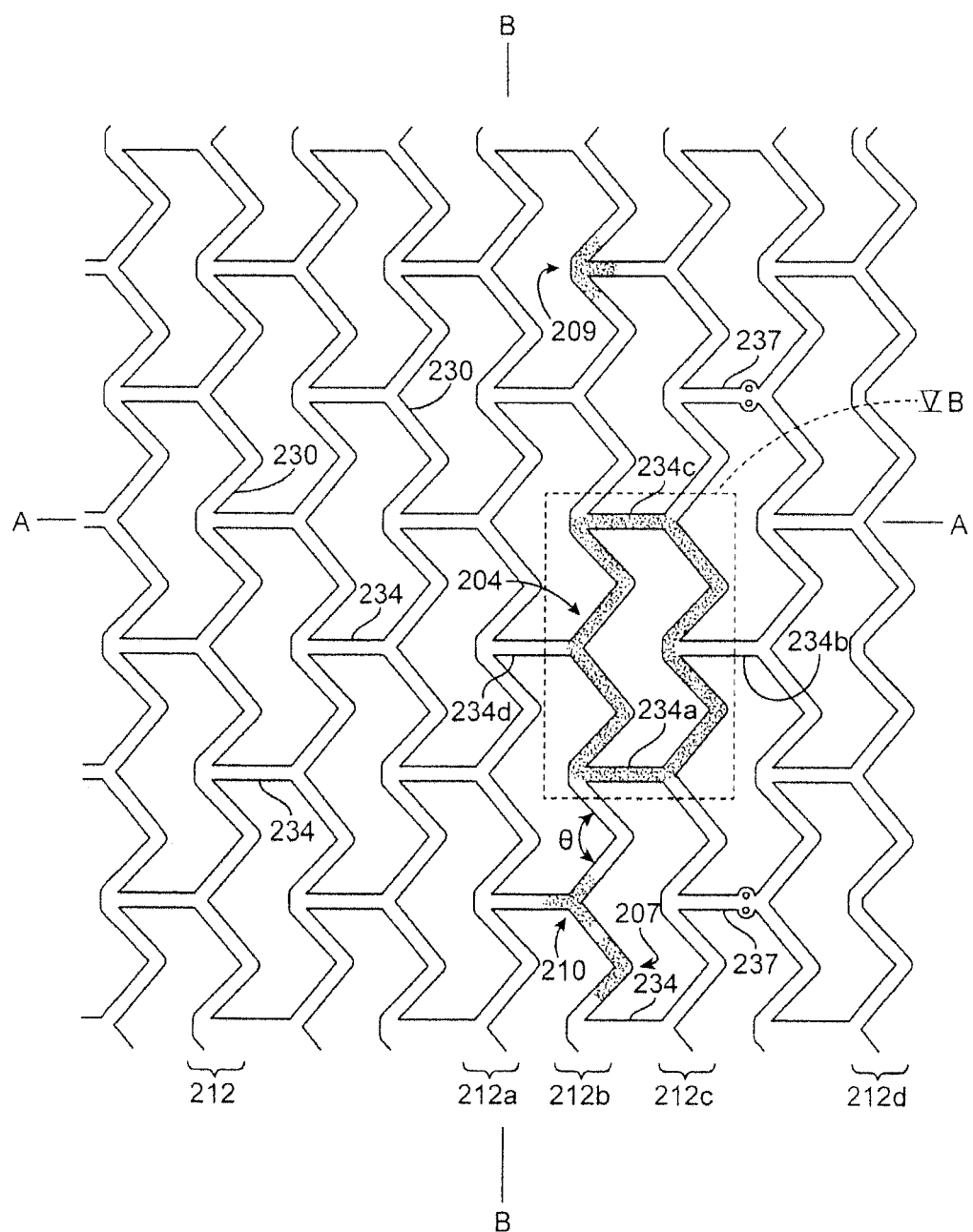
FIG. 2 depicts a first embodiment of a crush recoverable scaffold pattern.
Figure 3:
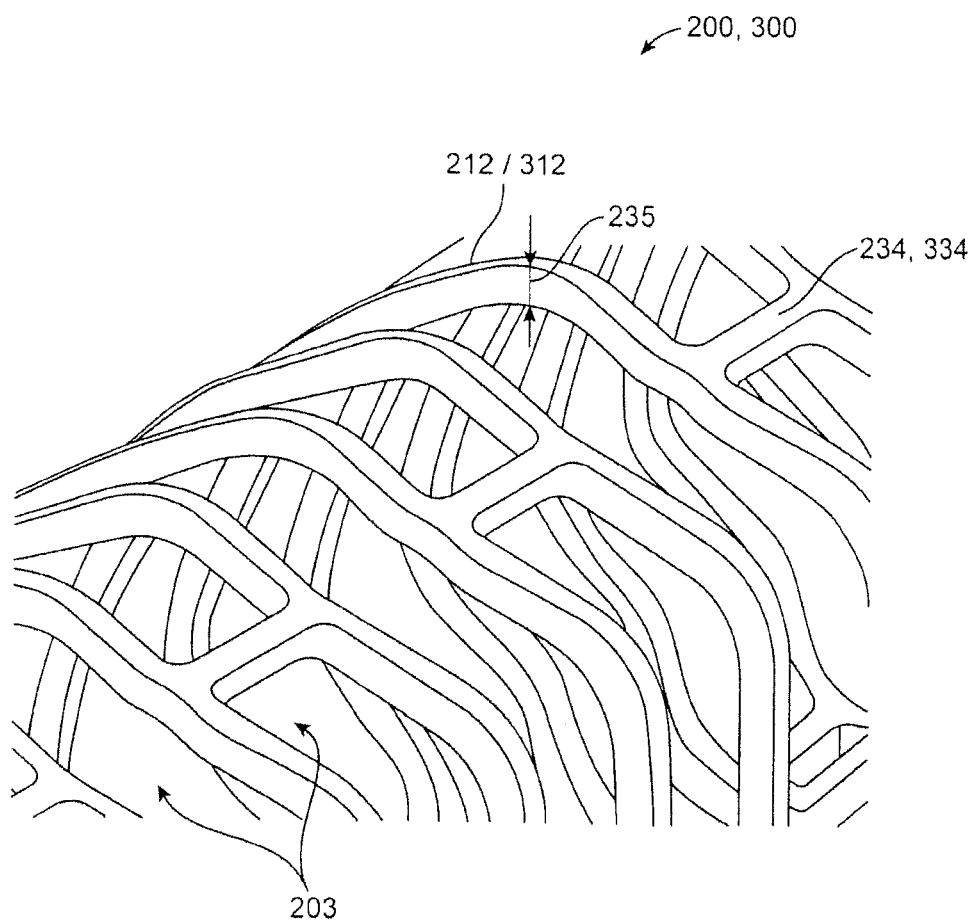
FIG. 3 is a partial perspective view of a scaffold structure.

A first embodiment of a crush recoverable scaffold pattern is depicted in FIG. 2. FIG. 2 depicts the pattern 200 which includes longitudinally-spaced rings 212 formed by struts 230. The pattern 200 of FIG. 2, represents a tubular scaffold structure (as partially shown in three dimensional space in FIG. 3), so that an axis A-A is parallel to the central or longitudinal axis of the scaffold. FIG. 3 shows the scaffold in a state prior to crimping or after deployment. As can be seen from FIG. 3, the scaffold comprises an open framework of struts and links that define a generally tubular body. A cylindrical tube of may be formed into this open framework of struts and links described in FIG. 2.

In FIG. 2, a ring 212 is connected to an adjacent ring by several links 234, each of which extends parallel to axis A-A. In this first embodiment of a scaffold pattern (pattern 200) four links 234 connect the interior ring 212, which refers to a ring having a ring to its left and right in FIG. 2, to each of the two adjacent rings. Thus, ring 212b is connected by four links 234 to ring 212c and four links 234 to ring 212a. Ring 212d is an end ring connected to only the ring to its left in FIG. 2.

A ring 212 is formed by struts 230 connected at crowns 207, 209 and 210. A link 234 is joined with struts 230 at a crown 209 (W-crown) and at a crown 210 (Y-crown). A crown 207 (free-crown) does not have a link 234 connected to it. Preferably the struts 230 that extend from a crown 207, 209 and 210 at a constant angle from the crown center, i.e., the rings 212 are approximately zig-zag in shape, as opposed to sinusoidal for pattern 200, although in other embodiments a ring having curved struts is contemplated. As such, in this embodiment a ring 212 height, which is the longitudinal distance between adjacent crowns 207 and 209/210 may be derived from the lengths of the two struts 230 connecting at the crown and a crown angle θ. In some embodiments the angle θ at different crowns will vary, depending on whether a link 234 is connected to a free or unconnected crown, W-crown or Y-crown.

The zig-zag variation of the rings 212 occurs primarily about the circumference of the scaffold (i.e., along direction B-B in FIG. 2). The struts 212 centroidal axes lie primarily at about the same radial distance from the scaffold's longitudinal axis. Ideally, substantially all relative movement among struts forming rings also occurs axially, but not radially, during crimping and deployment. Although, as explained in greater detail, below, polymer scaffolds often times do not deform in this manner due to misalignments and/or uneven radial loads being applied.

The rings 212 are capable of being collapsed to a smaller diameter during crimping and expanded to a larger diameter during deployment in a vessel. According to one aspect of the disclosure, the pre-crimp diameter (e.g., the diameter of the axially and radially expanded tube from which the scaffold is cut) is always greater than a maximum expanded scaffold diameter that the delivery balloon can, or is capable of producing when inflated. According to one embodiment, a pre-crimp diameter is greater than the scaffold expanded diameter, even when the delivery balloon is hyper-inflated, or inflated beyond its maximum use diameter for the balloon-catheter.

Pattern 200 includes four links 237 (two at each end, only one end shown in FIG. 2) having structure formed to receive a radiopaque material in each of a pair of transversely-spaced holes formed by the link 237. These links are constructed in such a manner as to avoid interfering with the folding of struts over the link during crimping, which, as explained in greater detail below, is necessary for a scaffold capable of being crimped to a diameter of about at most Dmin or for a scaffold that when crimped has virtually no space available for a radiopaque marker-holding structure.

Figure 4:
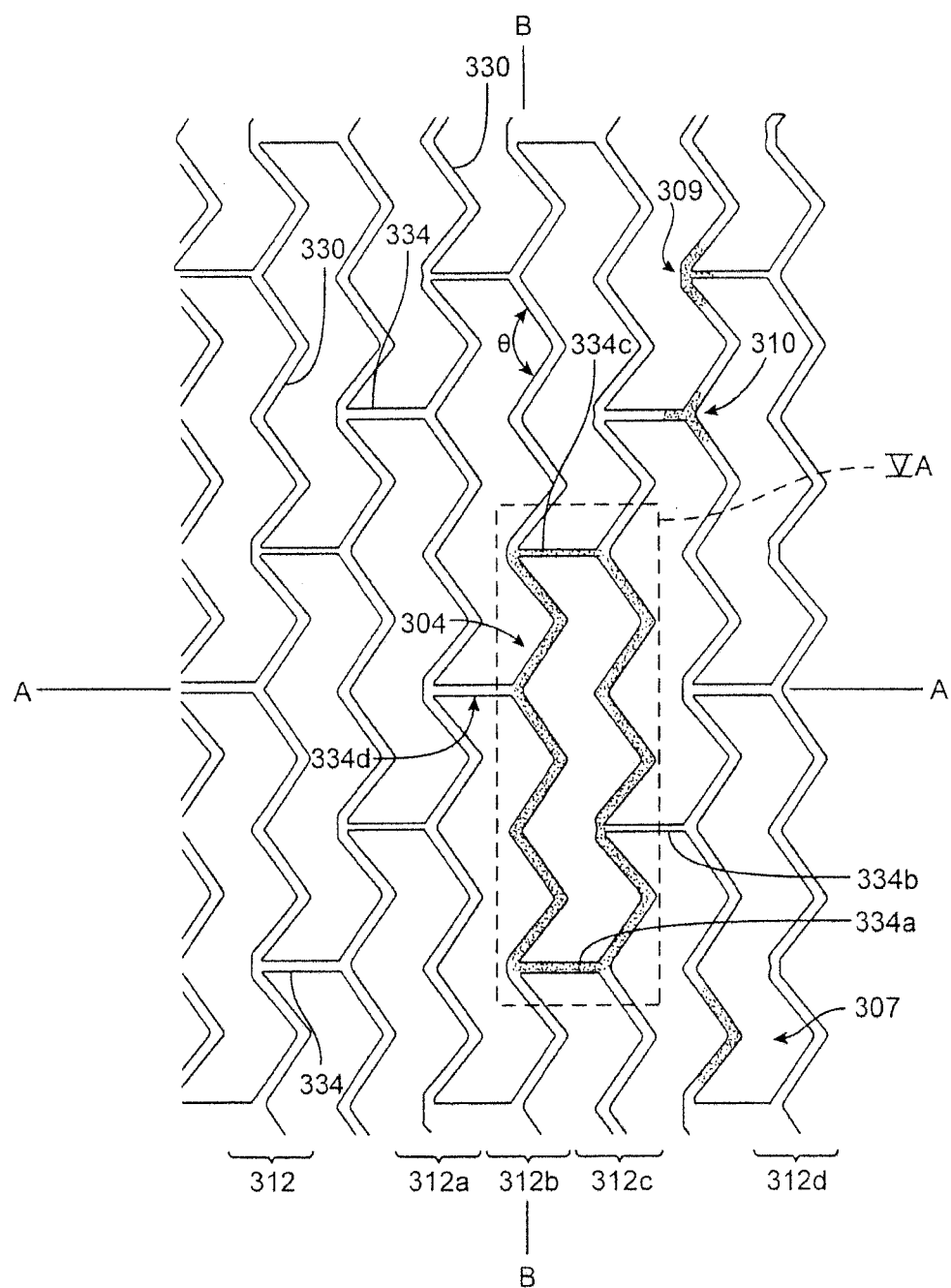
FIG. 4 depicts a second embodiment of a crush-recoverable scaffold structure.

A second embodiment of a crush-recoverable scaffold structure has the pattern 300 illustrated in FIG. 4. Like the pattern 200, the pattern 300 includes longitudinally-spaced rings 312 formed by struts 330. A ring 312 is connected to an adjacent ring by several links 334, each of which extends parallel to axis A-A. The description of the structure associated with rings 212, struts 230, links 234, and crowns 207, 209, 210 in connection with FIG. 2, above, also applies to the respective rings 312, struts 330, links 334 and crowns 307, 309 and 310 of the second embodiment, except that in the second embodiment there are only three struts 334 connecting each adjacent pair of rings, rather than four. Thus, in the second embodiment the ring 312b is connected to the ring 312c by only three links 334 and to the ring 312a by only three links 334. A link formed to receive a radiopaque marker, similar to link 237, may be included between 312c and ring 312d.

Figure 5A:
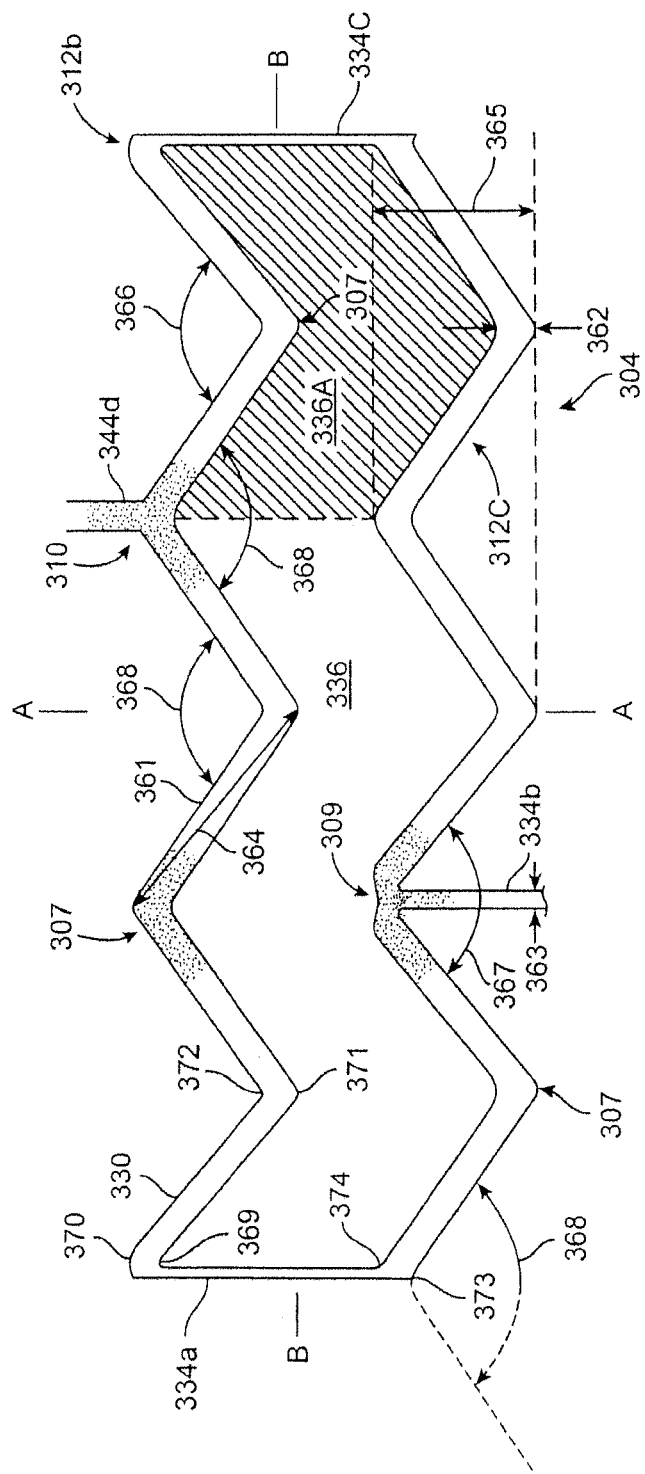
FIG. 5A depicts aspects of the repeating pattern of closed cell elements associated with the pattern of FIG. 4.
Figure 5B:
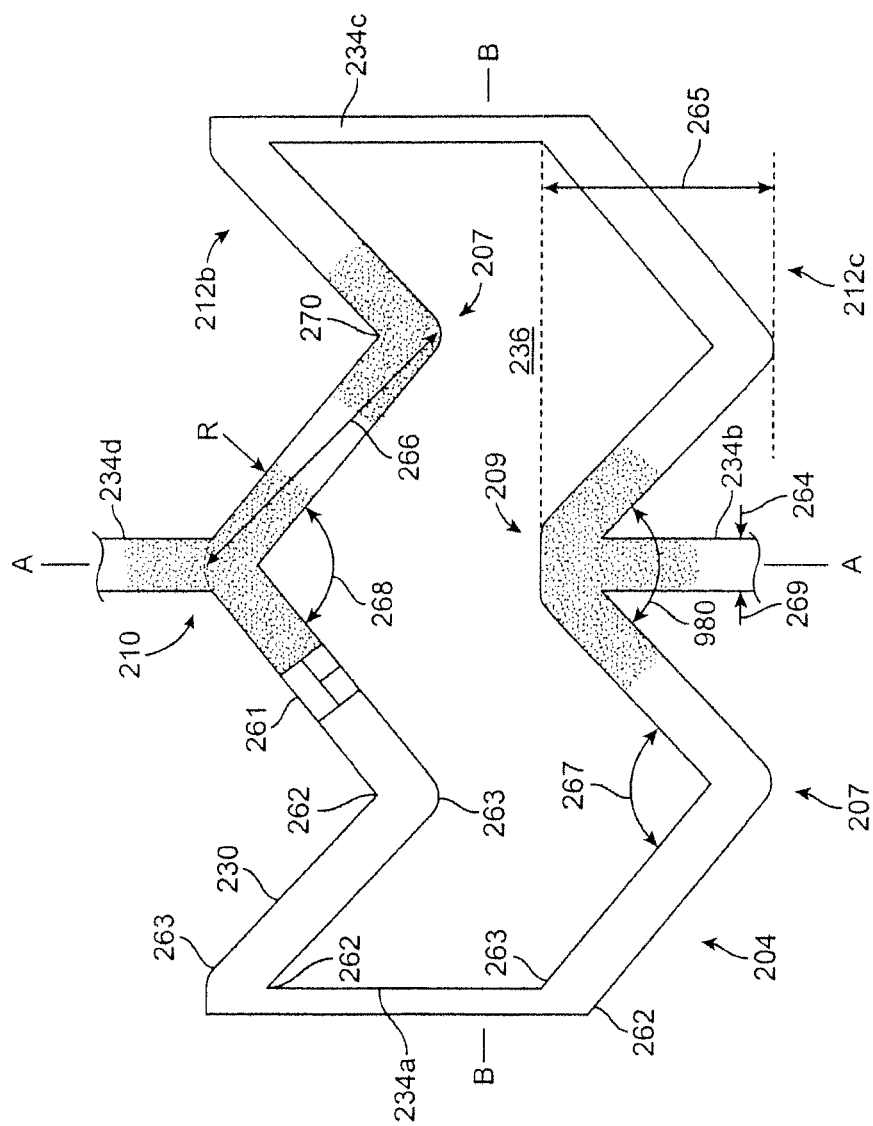
FIG. 5B depicts aspects of the repeating pattern of closed cell elements associated with the pattern of FIG. 2.

FIGS. 5A and 5B depict aspects of the repeating pattern of closed cell elements associated with each of the patterns 300 and 200, respectively. FIG. 5A shows the portion of pattern 300 bounded by the phantom box VA and FIG. 5B shows the portion of pattern 200 bounded by the phantom box VB. Therein are shown cell 304 and cell 204, respectively. In FIGS. 5A, 5B the vertical axis reference is indicated by the axis B-B and the longitudinal axis A-A. There are four cells 204 formed by each pair of rings 212 in pattern 200, e.g., four cells 204 are formed by rings 212b and 212c and the links 234 connecting this ring pair, another four cells 204 are formed by rings 212a and 212b and the links connecting this ring pair, etc. In contrast, there are three cells 304 formed by a ring pair and their connecting links in pattern 300.

Referring to FIG. 5A, the space 336 and 336a of cell 304 is bounded by the longitudinally spaced rings 312b and 312c portions shown, and the circumferentially spaced and parallel links 334a and 334c connecting rings 312b and 312c. Links 334b and 334d connect the cell 304 to the right and left adjacent ring in FIG. 3, respectively. Link 334b connects to cell 304 at a W-crown 309. Link 334d connects to cell 304 at a Y-crown 310. A "W-crown" refers to a crown where the angle extending between a strut 330 and the link 336 at the crown 310 is an obtuse angle (greater than 90 degrees). A "Y-crown" refers to a crown where the angle extending between a strut 330 and the link 336 at the crown 309 is an acute angle (less than 90 degrees). The same definitions for Y-crown and W-crown also apply to the cell 204. There are eight connected or free crowns 307 for cell 304, which may be understood as eight crowns devoid of a link 334 connected at the crown. There are one or three free crowns between a Y-crown and W-crown for the cell 304.

Additional aspects of the cell 304 of FIG. 5A include angles for the respective crowns 307, 309 and 310. Those angles, which are in general not equal to each other (see e.g., FIG. 6A for the "V2" and "V23" embodiments of scaffold having the pattern 300), are identified in FIG. 5A as angles 366, 367 and 368, respectively associated with crowns 307, 309 and 310. For the scaffold having the pattern 300 the struts 330 have strut widths 361 and strut lengths 364, the crowns 307, 309, 310 have crown widths 362, and the links 334 have link widths 363. Each of the rings 312 has a ring height 365. The radii at the crowns are, in general, not equal to each other. The radii of the crowns are identified in FIG. 5A as radii 369, 370, 371, 372, 373 and 374.

Cell 304 may be thought of as a W-V closed cell element. The "V" portion refers to the shaded area 336a that resembles the letter "V" in FIG. 6A. The remaining unshaded portion 336, i.e., the "W" portion, resembles the letter "W".

Referring to FIG. 5B, the space 236 of cell 204 is bounded by the portions of longitudinally spaced rings 212b and 212c as shown, and the circumferentially spaced and parallel links 234a and 234c connecting these rings. Links 234b and 234d connect the cell 204 to the right and left adjacent rings in FIG. 2, respectively. Link 234b connects to cell 236 at a W-crown 209. Link 234d connects to cell 236 at a Y-crown 210. There are four crowns 207 for cell 204, which may be understood as four crowns devoid of a link 234 connected at the crown. There is only one free crown between each Y-crown and W-crown for the cell 204.

Additional aspects of the cell 204 of FIG. 5B include angles for the respective crowns 207, 209 and 210. Those angles, which are in general not equal to each other (see e.g., FIG. 6B for the "V59" embodiment of a scaffold having the pattern 200), are identified in FIG. 5B as angles 267, 269 and 268, respectively associated with crowns 207, 209 and 210. For the scaffold having the pattern 200 the struts 230 have strut widths 261 and strut lengths 266, the crowns 207, 209, 210 have crown widths 270, and the links 234 have link widths 261. Each of the rings 212 has a ring height 265. The radii at the crowns are, in general, not equal to each other. The radii of the crowns are identified in FIG. 5A as inner radii 262 and outer radii 263.

Cell 204 may be thought of as a W closed cell element. The space 236 bounded by the cell 204 resembles the letter "W".

Comparing FIG. 5A to FIG. 5B one can appreciate that the W cell 204 is symmetric about the axes B-B and A-A whereas the W-V cell 304 is asymmetric about both of these axes. The W cell 204 is characterized as having no more than one crown 207 between links 234. Thus, a Y-crown crown or W-crown is always between each crown 207 for each closed cell of pattern 200. In this sense, pattern 200 may be understood as having repeating closed cell patterns, each having no more than one crown that is not supported by a link 234. In contrast, the W-V cell 304 has three unsupported crowns 307 between a W-crown and a Y-crown. As can be appreciated from FIG. 5A, there are three unsupported crowns 307 to the left of link 334d and three unsupported crowns 307 to the right of link 334b.

Figure 7:
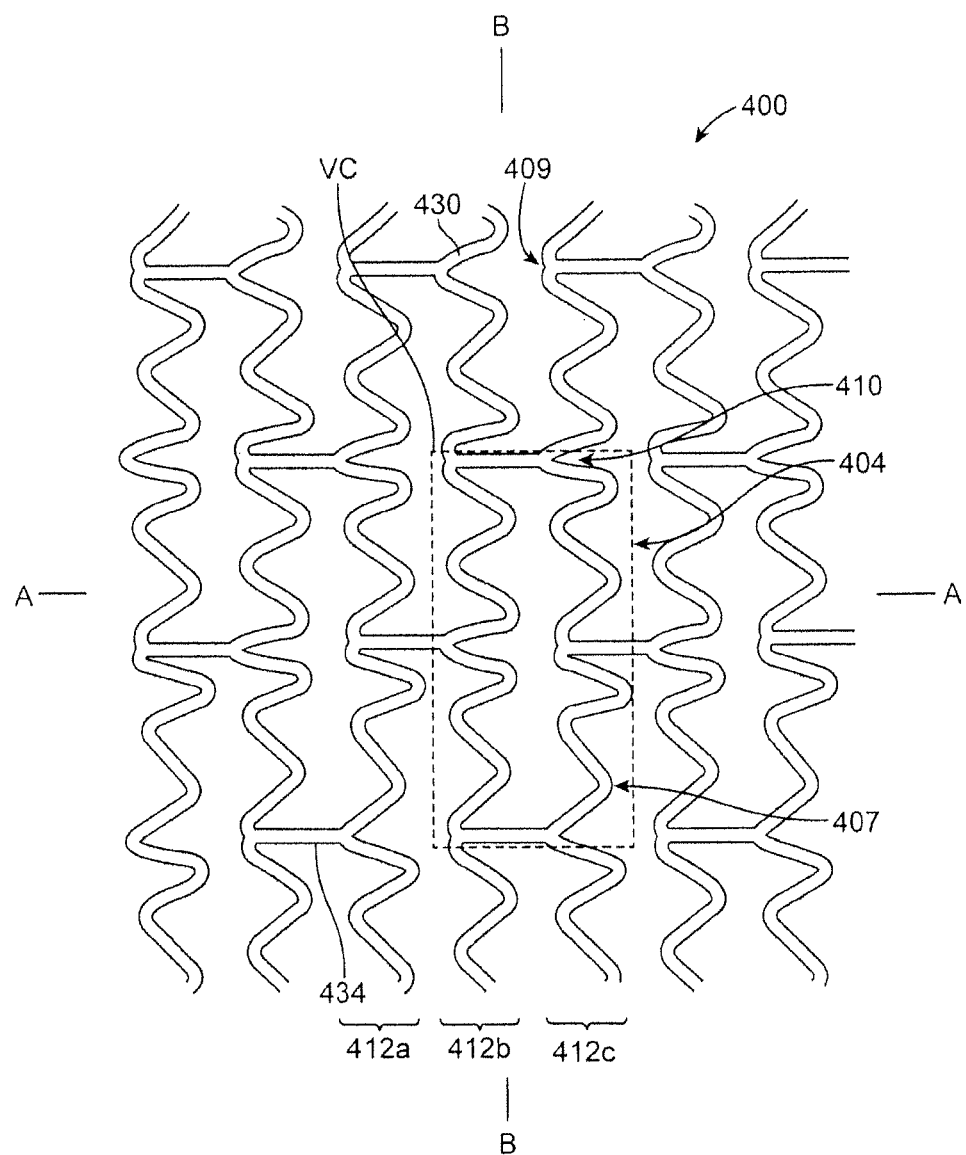
FIG. 7 depicts a third embodiment of a crush-recoverable scaffold structure.

A third embodiment of a crush-recoverable scaffold structure (referred to herein as "V79") has the pattern 400 illustrated in FIG. 7. Pattern 400 is an image of a portion of a scaffold post deployment which was generated the Visicon Finescan™ Stent Inspection System, and is discussed in detail in the Examples. Therefore, there is apparent a certain amount of distortion in the angles between the various struts. Like the patterns 200 and 300, the pattern 400 includes longitudinally-spaced rings 412 formed by struts 430. A ring 412 is connected to an adjacent ring by links 434, each of which extends parallel to axis A-A. The description of the structure associated with rings 212, struts 230, links 234, and crowns 207, 209, 210 in connection with FIG. 2, above, also applies to the respective rings 412, struts 430, links 434 and crowns 407, 409 and 410 of the third embodiment, except that in the third embodiment there are only two struts 434 connecting each adjacent pair of rings, rather than four. Thus, in the third embodiment the ring 412b is connected to the ring 412c by only two links 434 and to the ring 412a by only two links 434.

The sequence of crests starting at a W-crown and going around a circumference of a ring is: W-crown, 3-free crowns, Y-crown, 3 free crowns, W-crown, etc. The pattern shown in FIG. 7 has 2 W-crowns and 2-Y crowns. Thus, there are either 2 or 3 free crowns between a W-crown and Y-crown. A link formed to receive a radiopaque marker, similar to link 237, may be included between two rings.

Figure 8:
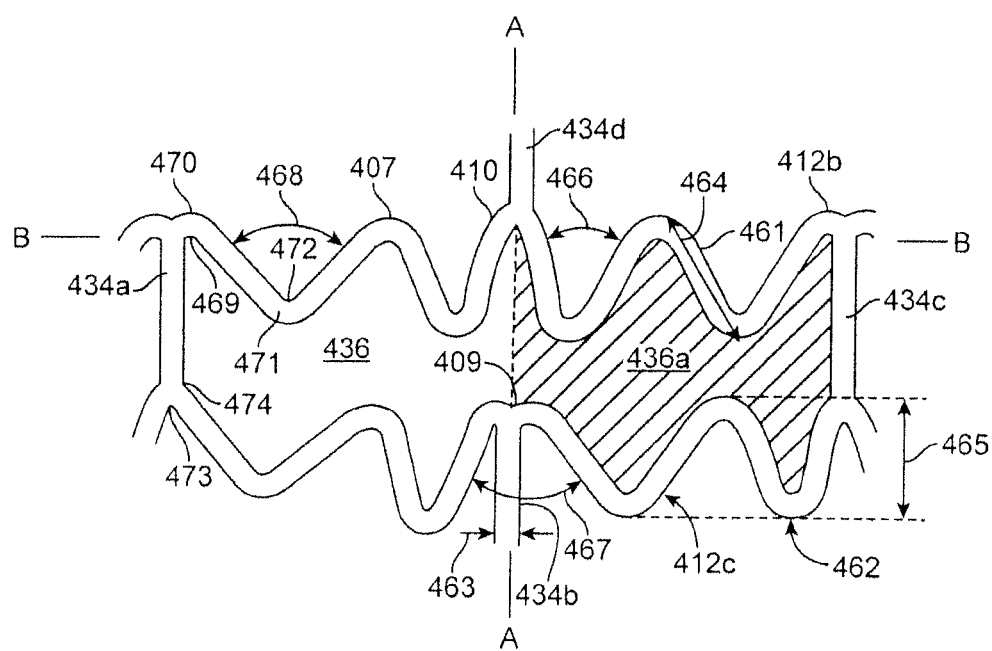
FIG. 8 depicts aspects of the repeating pattern of closed cell elements associated with the pattern of FIG. 7.

FIG. 8 shows the portion of pattern 400 bounded by the phantom box VC. Therein are shown cell 404. In FIG. 8, the vertical axis reference is indicated by the axis B-B and the longitudinal axis A-A. There are two cells 404 formed by each pair of rings 412 in pattern 400, e.g., two cells 404 are formed by rings 412b and 412c and the links 434 connecting this ring pair, another two cells 404 are formed by rings 412a and 412b and the links connecting this ring pair, etc.

Referring to FIG. 8, the space 436 and 436a of cell 404 is bounded by the longitudinally spaced rings 412b and 412c portions shown, and the circumferentially spaced and parallel links 434a and 434c connecting rings 412b and 412c. Links 434b and 434d connect the cell 404 to the right and left adjacent ring in FIG. 7, respectively. Link 434b connects to cell 404 at a W-crown 409. Link 434d connects to cell 404 at a Y-crown 410. There are 12 unconnected or free crowns 407 for cell 404, which may be understood as 12 crowns devoid of a link 434 connected at the crown. There are three free crowns between a Y-crown and W-crown for the cell 404.

Additional aspects of the cell 404 of FIG. 8 include angles for the respective crowns 407, 409 and 410. Those angles, which are in general not equal to each other (see e.g., FIG. 6A for the "V2" and "V23" embodiments of scaffold having the pattern 300), are identified in FIG. 8 as angles 466, 467 and 468, respectively associated with crowns 407, 409 and

410. For the scaffold having the pattern 400 the struts 430 have strut widths 461 and strut lengths 464, the crowns 407, 409, 410 have crown widths 462, and the links 434 have link widths 463. Each of the rings 412 has a ring height 465. The radii at the crowns are, in general, not equal to each other. The radii of the crowns are identified in FIG. 8 as radii 469, 470, 471, 472, 473 and 474.

Cell 404 may be thought of as a W-W closed cell element. The unshaded area 436 and unshaded area 436a each resemble the letter "W".

As described above, crush recoverable copolymer scaffolds also exhibit self-expansion or shape memory properties when in a physiological environment. The copolymer crush-recoverable scaffolds may self expand after expansion to a target diameter. The deployed scaffold may have a residual outward force applied the vessel wall due to the shape memory properties. The self expanding properties result in no or reduced recoil after expansion to the target diameter. The recoil may be less than 1 or 2%.

The crush recoverable copolymer scaffolds have greater fracture resistance than a PLLA scaffold. In particular, the inventors have found that copolymer scaffolds have few or no fractures when expanded from a crimped diameter to an expanded target diameter, for example, 8 to 10 mm. In addition, the crush recoverable copolymer scaffolds would have fewer fractured or broken struts during a time after implantation based on axial and bending fatigue data for such scaffolds.

As indicated above, the rubbery polymer of the copolymer has a tendency to decrease the radial strength and radial stiffness of the scaffolds. The composition of the rubbery polymer in the copolymer of the crush recoverable scaffold is such that the scaffold has the desired radial strength and radial stiffness while also exhibiting the shape memory properties with reduced or no recoil from the target diameter, desired crush recoverability, and shape memory properties. The composition the copolymer of the crush recoverable scaffolds may be 0.1 to 10 mol %, 1 to 10 mol %, 0.1 to 5 mol %, 3 to 5 mol %, 5 to 10 mol %, or 8 to 10 mol %.

The stent scaffolds may be formed by extruding polymer tubes made of the copolymer and laser cutting the tubes to form a scaffold. The fabrication methods of a bioabsorable stents described herein can include the following steps:
 (1) forming a polymeric tube using extrusion,
 (2) radially deforming the formed tube,
 (3) forming a stent scaffolding from the deformed tube by laser machining a stent pattern in the deformed tube with laser cutting,
 (4) optionally forming a therapeutic coating over the scaffolding,
 (5) crimping the stent over a delivery balloon, and
 (6) sterilization with election-beam (E-Beam) radiation.

In the extrusion step, a polymer is processed in an extruder above the melting temperature of the copolymer.

In step (2) above, the extruded tube may be radially deformed to increase the radial strength of the tube, and thus, the finished stent. The increase in strength reduces the thickness of the struts required to support a lumen with the scaffold when expanded at an implant site. In exemplary embodiments, the strut thickness can be 100-200 microns, or more narrowly, 120-180, 140-160, or 160-200 microns.

Detailed discussion of the manufacturing process of a bioabsorbable stent can be found elsewhere, e.g., U.S. Patent Publication Nos. 20070283552 and 20120073733 which are incorporated by reference herein.

"Molecular weight refers to either number average molecular weight (Mn) or weight average molecular weight (Mw). References to molecular weight herein refer to either Mn or Mw, unless otherwise specified.

"Semi-crystalline polymer" refers to a polymer that has or can have regions of crystalline molecular structure and amorphous regions. The crystalline regions may be referred to as crystallites or spherulites which can be dispersed or embedded within amorphous regions.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility.

The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" and "stiffness" may be defined as the ratio of a component of stress or force per unit area applied to a material divided by the strain along an axis of applied force that results from the applied force. The modulus or the stiffness typically is the initial slope of a stress-strain curve at low strain in the linear region. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, P A, 1989).

EXAMPLES

Scaffold samples were prepared with two poly(L-lactide-co-caprolactone) molar compositions of PLLA/PCL, 90:10 and 90:5. For comparison, PLLA scaffold samples were also prepared. The samples were tested after e-beam sterilization. Scaffolds with a poly(DL-lactide)/Everolimus coating were also tested. All scaffold samples were the V79 pattern.

Processing:

90:10 PLLA-PCL with intrinsic viscosity (IV) of 3.2 was processed by extrusion (water content 310 ppm, temp approximately 380 deg F.) to form a tube with 0.059 in ID. The tube was expanded to 8 mm OD at a temperature above its Tg but lower than Tm. It was then laser cut into a V79 scaffold pattern. L-lactide monomer content in extruded tubing and expanded tubing was 0.12%.

95:5 PLLA-PCL with IV of 3.8 was processed by extrusion (water content 320 ppm, temp approximately 370 deg F.) to form a tube with 0.051 in ID. The tube was then expanded to 7 mm OD at a temperature above its Tg but lower than Tm. It was then laser cut into a V79 scaffold pattern. L-lactide monomer content in extruded tubing and expanded tubing was 0.11%.

The scaffold samples were crimped onto a folded Omnilink Elite PTA balloons (Abbott Vascular Inc., Santa Clara, Calif.) at 48 deg C., packaged, and sterilized by e-beam.

Molecular Weight:

The Mn of the 90:10 expanded tubing sample was approximately 150 kDa and the Mn and of sterilized scaffold was approximately 68 kDa. The Mn of the 95:5 expanded tubing sample was approximately 100 kDa and the Mn and of sterilized scaffolds was 82 kDa.

Scaffold Dislodgement Force:

A scaffold dislodgement force for a scaffold crimped to a balloon refers to the maximum force applied to the scaffold along its longitudinal axis that the scaffold is able to resist before dislodging from the balloon. Scaffold dislodgement force for the samples was measured by a tape test. The scaffold dislodgement force for the 90:10 samples was 1.34±0.35 lb and the 95:5 samples was 1.00±0.10 lb.

Radial Strength and Stiffness

Figure 9:
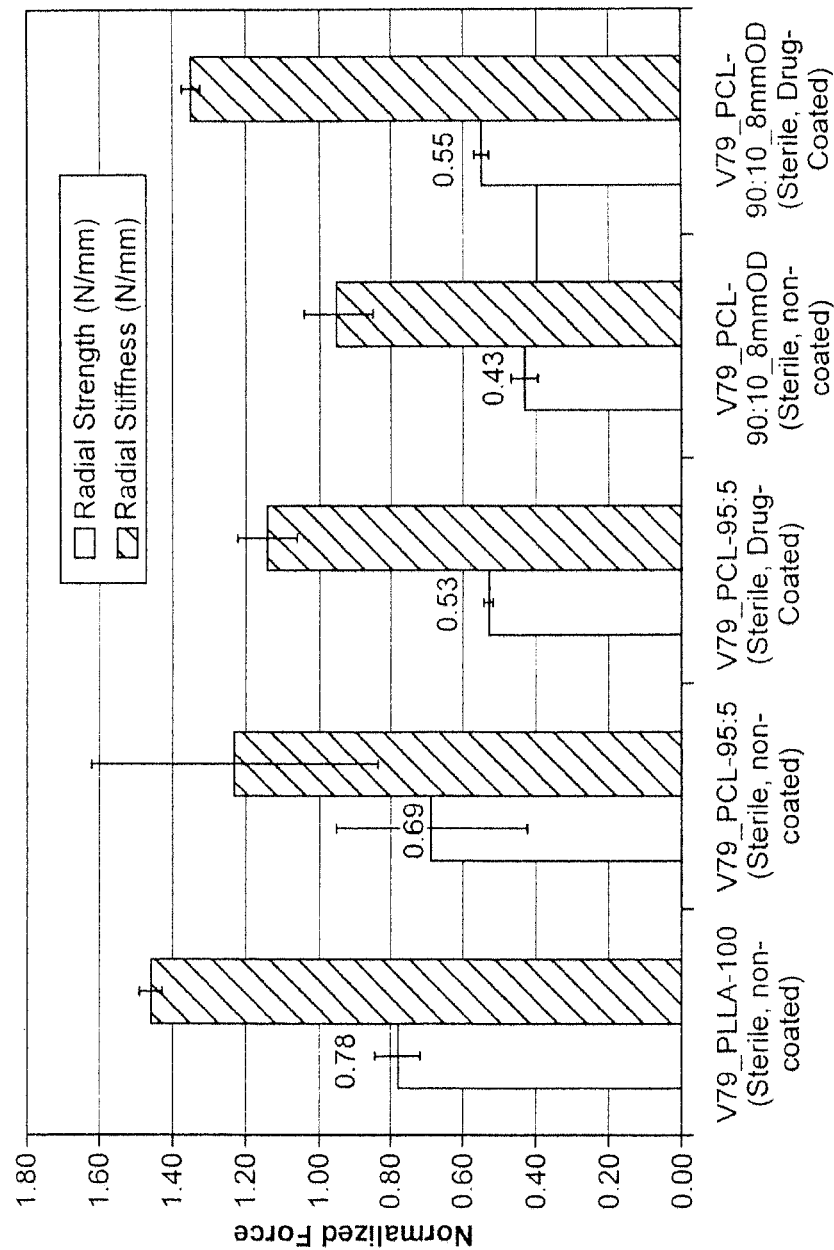
FIG. 9 shows the radial strength and stiffness for scaffold samples.

Radial strength and stiffness were measured on an MSI tester (Machines Solutions Inc., Flagstaff, Ariz.) and radial strength for each composition was greater than 0.4 N/mm. FIG. 9 shows the radial strength and stiffness for PLLA scaffolds, 95:5 PLLA-PCL uncoated scaffolds, 95:5 PLLA-PCL coated scaffolds, 90:10 PLLA-PCL uncoated scaffolds, and 90:10 PLLA-PCL uncoated scaffolds.

Post-Dilation to Fraction:

The scaffold samples were dilated from the crimped diameter and the minimum OD at fracture was observed. As shown in Table 2, both 95:5 and 90:10 scaffolds demonstrated a significantly higher fracture diameter than the PLLA scaffold theoretical fracture diameter of 9.6 mm.

TABLE 2

Post-Dilation to fracture of scaffolds.

| Scaffold Type | Post-Dilation to Fracture (mm) |
| --- | --- |
| PLLA | 9.6 mm (theoretical) |
| 95:5 PLLA-PCL | 10.0 +/− 0.1 mm. |
| 90:10 PLLA-PCL | 10.7 +/− 0.8 mm. |

Figure 10:
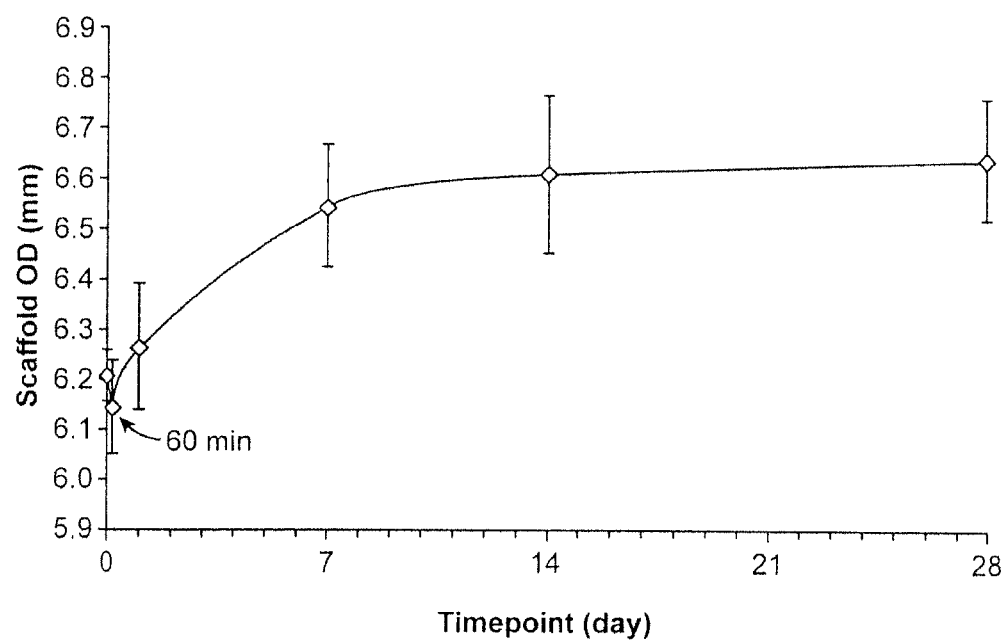
FIG. 10 shows the diameter of a 90:10 PLLA-PCL scaffold as a function of time after expansion.

Recoil:

The inward and outward recoil of the 90:10 PLLA-PCL scaffold was studied. The scaffold was balloon expanded to 6 mm, the balloon was deflated and then the scaffold diameter was recorded with time. FIG. 10 shows the diameter of the scaffold as a function of time after expansion. The diameter recoiled inward for about the first 60 min followed by recoil outward with a significant OD growth as a function of time at least up to 28 days.

Figure 11:
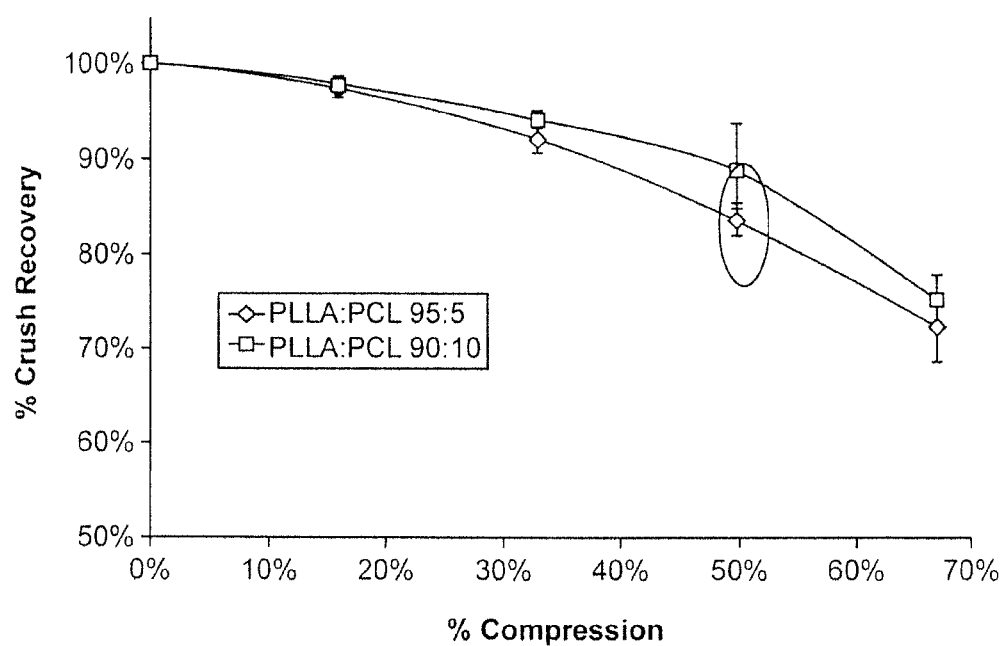
FIG. 11 depicts crush recovery results for 95:5 PLLA-PCL and 90:10 PLLA-PCL scaffolds.

Crush Recovery:

The crush recovery of the PLLA and 90:10 PLLA-PCL scaffolds were tested. FIG. 11 shows the results for both of the scaffolds.

Axial Fatigue:

The PLLA, 95:5 PLLA-PCL, and 90:10 PLLA-PCL scaffolds were subjected to axial fatigue testing.

The scaffolds coated with silicone sealant were deployed inside silicone tubing with two different hardnesses. The samples were dried for 24 hours and the tubes were stretched axially by 7%. The scaffold samples were then subjected to 500k cycles at 1 Hz in circulating water at 37° C. The scaffold samples were inspected for fractures at different time points.

Figure 12:
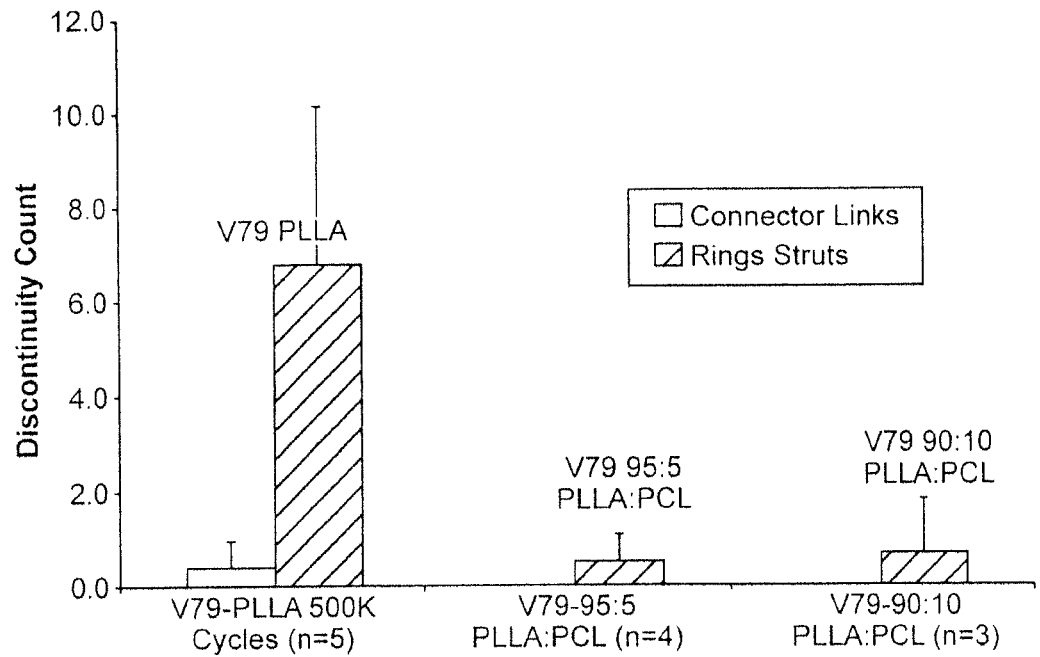
FIG. 12 shows discontinuity count in ring and connector links after axial fatigue testing for the PLLA, 95:5 PLLA-PCL, and 90:10 PLLA-PCL scaffolds.
Figure 13:
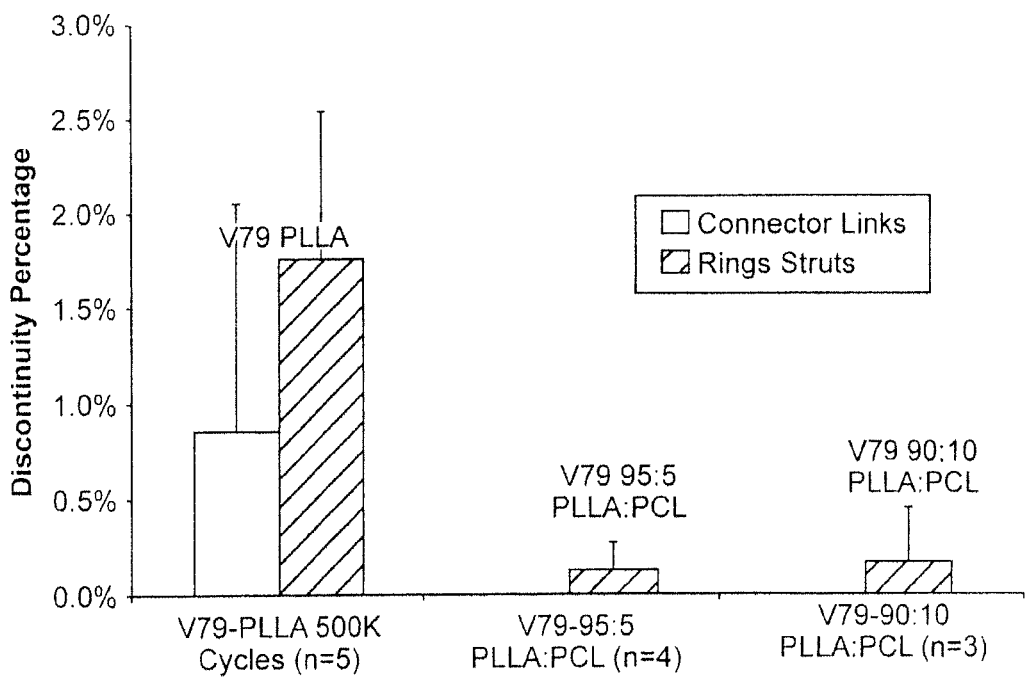
FIG. 13 shows discontinuity percentage in ring and connector links after axial fatigue testing for the PLLA, 95:5 PLLA-PCL, and 90:10 PLLA-PCL scaffolds.

The results demonstrated the PLLA-PCL scaffolds had reduced scaffold discontinuities at 500K cycles compared to PLLA. FIG. 12 shows discontinuity count in ring and connector links for each scaffold. FIG. 13 shows discontinuity percentage in ring and connector links for each scaffold.

Imaging of Scaffolds Post Deployment

Images of the scaffolds post deployment were generated the Visicon Finescan™ Stent Inspection System, Visicon Inspection Technologies, LLC (Napa, Calif.). The system employs a scan camera to generate a flat, unrolled view of a scaffold. In operation, the scaffold is mounted on a mandrel with a fine diffuse surface. This mandrel is held under the linear array camera and rotated by the system electronics and is used to trigger the camera to collect a line of image data in a precise line-by-line manner.

Figure 14:
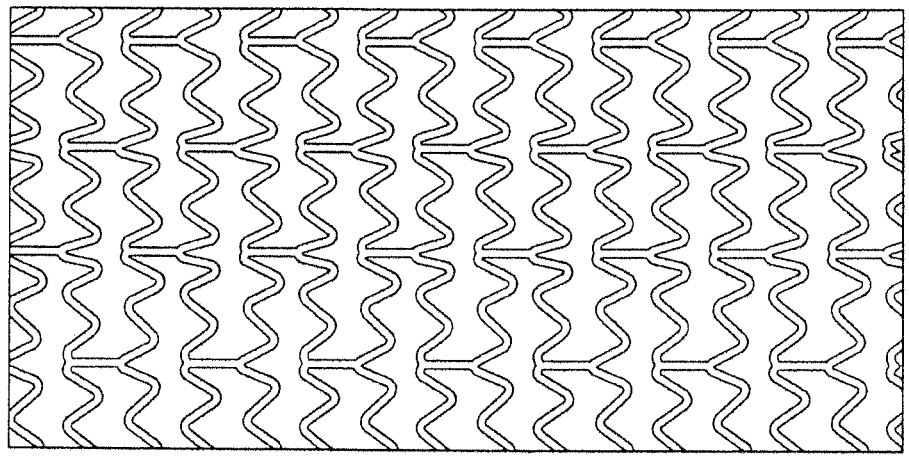
FIGS. 14 and 15 depict Finescan images of the 95:5 and the 90:10 PLLA-PCL scaffolds, respectively, post deployment.
Figure 15:
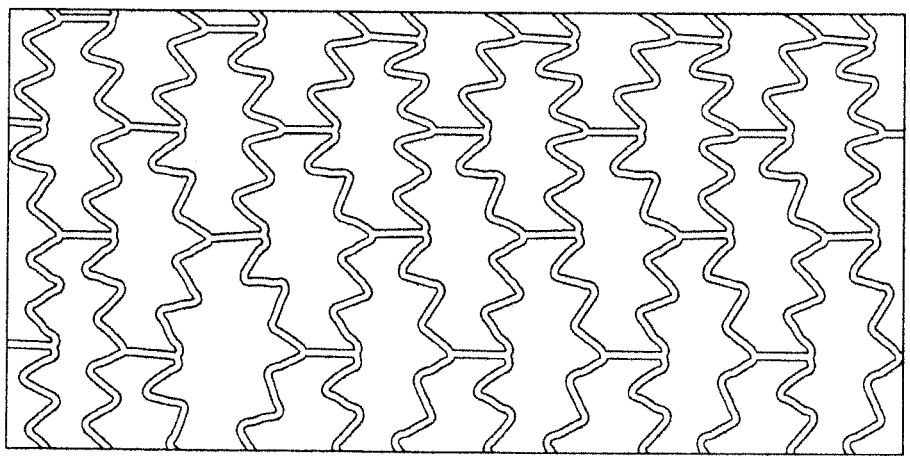

FIGS. 14 and 15 depict Finescan images of the 95:5 and the 90:10 PLLA-PCL scaffolds, respectively, post deployment. The 95:5 scaffold has minimal disruption in its structure.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A stent, comprising:

a scaffold formed from a polymer tube and configured for being crimped to a balloon, wherein the scaffold has a pattern of interconnected struts, and the scaffold is configured to have an expanded diameter when expanded from a crimped state by the balloon;

wherein the scaffold is configured to attain greater than about 80% of the expanded diameter after being crushed to 50% of the expanded diameter;

wherein the scaffold has a radial stiffness greater than 0.3 N/mm;

wherein the scaffold is made from a shape memory random copolymer of poly(L-lactide) (PLLA) and a rubbery polymer that is 0.1 to 10 wt % or mol % of the copolymer; and wherein the scaffold is configured to exhibit self-expanding properties at 37 deg C. in physiological conditions.

* * * * *